(12) United States Patent
Chen et al.

(10) Patent No.: US 9,604,945 B2
(45) Date of Patent: Mar. 28, 2017

(54) SYDNONIMINES-SPECIFIC DOPAMINE REUPTAKE INHIBITORS AND THEIR USE IN TREATING DOPAMINE RELATED DISORDERS

(71) Applicant: Caliper Life Sciences, Inc., Hopkinton, MA (US)

(72) Inventors: Hao Chen, Columbia, MD (US); Ming Liu, Rockville, MD (US); Qi Su, Columbia, MD (US); Manish Raisinghani, Jamesburg, NJ (US)

(73) Assignee: Caliper Life Sciences, Inc., Hopkinton, MA (US)

(*) Notice: Subject to any disclaimer, the term of this patent is extended or adjusted under 35 U.S.C. 154(b) by 0 days.

(21) Appl. No.: 13/851,359

(22) Filed: Mar. 27, 2013

(65) Prior Publication Data
US 2013/0281495 A1    Oct. 24, 2013

Related U.S. Application Data

(60) Division of application No. 13/180,996, filed on Jul. 12, 2011, now Pat. No. 8,415,385, which is a continuation of application No. 12/048,334, filed on Mar. 14, 2008, now abandoned.

(60) Provisional application No. 60/894,739, filed on Mar. 14, 2007.

(51) Int. Cl.
*C07D 271/04*    (2006.01)
*A61K 31/4245*   (2006.01)

(52) U.S. Cl.
CPC ........ *C07D 271/04* (2013.01); *A61K 31/4245* (2013.01)

(58) Field of Classification Search
CPC .......................... A61K 31/4245; C07D 271/04
USPC ....................................................... 514/364
See application file for complete search history.

(56) References Cited

U.S. PATENT DOCUMENTS

| 3,277,108 | A | 10/1966 | Daeniker |
| 4,245,100 | A | 1/1981 | Kholodov et al. |
| 4,277,609 | A | 7/1981 | Stein |
| 4,301,285 | A | 11/1981 | Stein |
| 4,371,539 | A | 2/1983 | Stein |
| 4,371,697 | A | 2/1983 | Stein |
| 4,446,322 | A | 5/1984 | Stein |
| 5,554,626 | A | 9/1996 | Moldt et al. |
| 2005/0176680 | A1 | 8/2005 | Lalji et al. |

FOREIGN PATENT DOCUMENTS

| CA | 1097659 | 3/1981 |
| DE | 2028880 | 12/1971 |
| GB | 1262830 | 2/1972 |
| WO | 81/00567 | 3/1981 |
| WO | 82/01187 | 4/1982 |

OTHER PUBLICATIONS

Al'tshuler et al. Farmakologiya I Toksikologiya 1980, 43, 153-158.*
English translation of Al'tshuler et al. Farmakologiya I Toksikologiya 1980, 43, 153-158.*
Krasov et al. Zhurnal Nevropatologii I Psikhiatrii Imeni S.S. Korsakova 1988, 88 (8): 97-101.*
English translation of Krasov et al. Zhurnal Nevropatologii I Psikhiatrii Imeni S.S. Korsakova 1988, 88 (8): 97-101.*
Temkov et al. Nevrologiya, Psikhiatriya I Nevrokhirurgiya 1975, 14, 179-183.*
English translation of Temkov et al. Nevrologiya, Psikhiatriya I Nevrokhirurgiya 1975, 14, 179-183.*
Definition for hyperdyanic syndrome provided by the Center for Cognitive-Developmental Assessment & Remediation (http://www.bgcenter.com/bgqa/medical9.htm), accessed Oct. 14, 2010.*
Wilens et al. Am. J. Psychiatry 1999, 156, 1931-1937.*
National Institute of Mental Health, Attention Deficit Hyperactivity Disorder, http://www.nimh.nih.gov/health/publications/attention-deficit-hyperactivity-disorder/complete-index.shtml, 2008.*
Lai et al. The Lancet, 2014, 383, 896-910.*
Nakasato et al. Brain Research 2008, 1193, 128-135.*
Gillberg et al. J. Autism Dev. Disord. 1983, 13, 383-396.*
McCracken et al. N. Engl. J. Med. 2002, 347, 314-321.*
Anderson et al. J. Autism Dev. Disord. 1989, 19, 227-239.*
Pietropaolo et al. PLoS ONE, 2011, 6(2), e17073.*
Cohen et al. Journal of Autism and Developmental Disorders 2005, 35, 103-116.*
Pierce et al. Biol. Psychiatry 2001, 49, 655-664.*
R. Gainetdinov et al., "Glutamatergic modulation of hyperactivity in mice lacking the dopamine transporter", PNAS, 98(20): 11047-11054 (2001).
F. Hall et al., "Sex-dependent Modulation of Ethanol Consumption in Vesicular Monoamine Transporter 2 (VMAT2) and Dopamine Transporter (DAT) Knockout Mice", Neuropsychopharmacology, 28: 620-628 (2003).
Y. Mateo et al., "Role of serotonin in cocaine effects in mice with reduced dopamine transporter function", PNAS, 101 (1): 372-377 (2004).
S. Izenwasser et al., "Differential Relationships Among Dopamine Transporter Affinities and Stimulant Potencies of Various Uptake Inhibitors", Eur. J. Pharmacol., 263: 277-83 (2004).
P. Kunko et al., "Alterations in Locomotor Activity during Chronic Cocaine Administration: Effect on Dopamine Receptors and Interaction with Opioids", J. Pharmacol. and Exp. Ther, 285(1): 277-84 (1998).

(Continued)

*Primary Examiner* — Matthew Coughlin
(74) *Attorney, Agent, or Firm* — Patrick J. Hagan; Dann, Dorfman, Herrell and Skillman

(57) ABSTRACT

Derivatives of Sydnonimine and its analogues, which bind selectively to dopamine transporter (DAT) proteins are useful for treating and delaying the progression of disorders and illnesses that are alleviated by inhibiting dopamine reuptake.

11 Claims, 18 Drawing Sheets

(56) References Cited

OTHER PUBLICATIONS

G. Campiani et al., "Synthesis and Pharmacological Evaluation of Potent and Highly Selective D3 Receptor Ligands: Inhibition of Cocaine-Seeking Behavior and the Role of Dopamine D3/D2 Receptors", J. Med. Chem., 46: 3822-3839 (2003).

F. J. Garcia-Ladona et al., "BP 897, a Selective Dopamine D3 Receptor Ligand with Therapeutic Potential for the Treatemnt of Cocaine-Addiction", CNS Drug Reviews, 9: 141-158 (2003).

S. Schlussman et al., "Locomotion, stereotype, and dopamine D1 receptors after chronic "binge" cocaine in C57BL/6J and 129/J mice", Pharmacol. Biochem. Behav., 75: 123-131 (2003).

D. Platt et al., "Suppression of cocaine—and food-maintained behavior by the D2-like receptor partial agonist terguride in squirrel monkeys", Psychopharmacology, 166: 298-305 (2003).

S. Vorel, "Dopamine D3 Receptor Antagonism Inhibits Cocaine-Seeking and Cocaine-Enhanced Brain Reward in Rats", J. Neurosci., 22(21): 9595-9603 (2002).

E. Ellinwood et al., "Effect of daily dosing duration of direct and indirect dopamine receptor agonists: cocaine cross-tolerance following chronic regimens", Eur Neuropsychopharmacol., 12: 407-15 (2002).

J. Owens et al., "Second generation SSRIS: human monoamine transporter binding profile of escitalopram and R-fluoxetine", Encephale, 28(4): 350-5 (2002).

A. Zhang et al., "Further Studies on Conformationally Constrained Tricyclic Tropane Analogues and Their Uptake Inhibition at Monoamine Transporter Sites: Synthesis of (Z)-9-(Substituted arylmethylene)-7-azatricyclo[4.3.1.0] decanes as a Novel Class of Serotonin Transporter Inhibitors", J. Med. Chem., 45: 1930-1941 (2002).

C. Sanchez eta l., "Escitalopram, the S-(+)enantionmer of citalopram, is a selective serotonin reuptake inhibitor with potent effects in animal models predictive of antidepressant and anxiolytic activities", Psychopharmacology, 167: 353-362 (2003).

E. Fish et al., "Anxiolytic-Like Effects of Escitalopram, Citalopram, and R-Citalopram in Maternally Separated Mouse Pups", J. Pharmacol. Exp. Ther., 308: 474-80 (2004).

N. Volkow et al., "Therapeutic Doses of Oral Methylphenidate Significantly Increase Extracellular Dopamine in the Human Brain", J. Neurosci., 21(2) RC 121 (2001).

P. D'Aquila et al., "The role of dopamine in the mechanism of action of antidepressant drugs", Eur. J. Pharmacol., 405: 365-373 (2000).

I. Sora et al., "Molecular mechanisms of cocaine reward: Combined dopamine and serotonin transporter knockouts eliminate cocaine place preference", PNAS, 98(9): 5300-5305 (2001).

J. Witkin et al., "Behavorial, Toxic, and Neurochemical Effects of Sydnocarb, a Novel Psychomotor Stimulant: Comparisons with Methamphetamine", J. Pharmacol. Exp. Ther., 288(3): 1298-1310 (1999).

I.S. Slyusarenko et al., "Sydnonimines prepared from E-aminocaproic acid", Khimiya Geterotsiklicheskikh Soedinenii, 11: 1469-72 (1973) CAPLUS record.

S. Erdo et al., Inhibition of Dopamine Uptake by a New Psychostimulant Mesocarb (Sydnocarb), Polish Journal of Pharmacology and Pharmacy, 33: 141-147 (1981), Abstract.

M. Thorpy, "Therapeutic advances in narcolepsy", Sleep Medicine, 8: 427-440 (2007).

L. E. Kholodov et al., "Sydnones and sydnonimines. XXXV. Salts and exocyclic derivatives of some sydnonimines", Zhurnal Organicheskoi Khimii, 3(8): 1513-1518 (1967) (CAPLUS record).

H. Takahashi et al., "The Role of Extrastriatal Dopamine D2 Receptors in Schizophrenia", Biol. Psychiatry, 59: 919-928 (2006).

L. E. Kholodov et al., "Synthesis and pharmacological activity of some 3-substituted sydnone imines", Khimiko-Farmatsevticheskii Zhurnal, 2(5): 3-7 (1968).

Z.A. Olovyanishnikova et al., "Electrophilic substitution in N-exocarbamoyl derivatives of sydnone imines", Khimiya Geterotsiklicheskikh Soedinenii, 9: 1198-203 (1975) (CAPLUS record).

Z.A. Olovyanishnikova et al., "Phenylethyl derivatives of sydnonimines", Khimiko-Farmatsevticheskii Zhurnal, 6 (6): 20-3 (1972).

Al'tshuler et al., Farmakologiya/Toksikologiya, 43: 153-158 (1980).

Definition for "acyl", Hawley's Condensed Chemical Dictionary, 14th edition (2002).

S. Izenwasser et al., "Differential relationships among dopamine transporter affinities and stimulant potencies of various uptake inhibitors", Eur. J. Pharmacol., 263: 277-283 (1994).

V.A. Krasov et al., "Sidnocarb Treatment of Young Schoolchildren with Hyperdynamic Syndrome", Zhurnal Nevropatologii I Psikhiatrii Imeni S.S. Korsakova, 88(8): 97-101 (1988).

English translation of Krasov et al., Zhurnal Nevropatologii/ Psikhiatrii Imeni S.S. Korsakova, 88(8): 97-101 (1988).

English translation of Al'tshuler et al., Farmakologiya/ Toksikologiya, 43: 153-158 (1980).

F. George, "Cocaine produces low dose locomotor depressant effects in mice", Psychopharmacology, 99: 147-150 (1989).

S.H. Heil et al., "Comparison of the subjective, physiological, and psychomotor effects of atomoxetine and methylphenidate in light drug users", Drug and Alcohol Dependence, 67: 149-156 (2002).

H. Mitchell et al., "The Effects of Norepinephrine Transporter Inactivation on Locomotor Activity in MIce", Biol. Psychiatry, 60: 1046-1052 (2006).

Japanese "Notification of Reason(s) for Refusal" issued Apr. 8, 2013 in corresponding JP Patent Application No. 2009-553801.

Antonawich, Francis J., "Nesting and shredding behavior as an indicator of hippocampal ischemic damage", Brain Research, 764: 249-252 (1997).

Baker, K.B. et al., "Male and female FMR1 knockout mice on C57 albino background exhibit spatial learning and memory impairments", Genes, Brain and Behavior, 9: 562-574 (2010).

Bernardet, Maude et al., "FMR1 KO Mice as a Possible Model of Autistic Features", The Scientific World Journal, 6: 1164-1176 (2006).

Demark, Jenny L., "The Relationship Between Autism and Fragile X Syndrome: A Review of the Research", Journal on Development Disabilities, 9(2): 29-43 (2002).

Hall, Scott S., "Treatments for Fragile X Syndrome: A Closer Look at the Data", Dev. Disabil. Res. Rev., 15(4): 353-360 (2009).

Hamilton, P.J. et al., "De novo mutation in the dopamine transporter gene associates dopamine dysfunction with autism spectrum disorder", Molecular Psychiatry, pp. 1-9 (2013).

Klemmer, Patricia et al., "Proteomics, Ultrastructure, and Physiology of Hippocampal Synapses in a Fragile X Syndrome Mouse Model Reveal Presynaptic Phenotype", J. Biol. Chem., 286: 25495-25504 (2011).

Nakamura, Kazuhilo et al., "Brain Serotonin and Dopamine Transporter Bindings in Adults with High-Functioning Autism", Arch. Gen. Psychiatry, 67(1): 59-68 (2010).

Saul, Robert A., et al., "FMR1-Related Disorders", GeneReviews, R.A. Pagon et al., Editors: Seattle (WA), First published Jun. 16, 1998.

Paul, Kush et al., "Dampened dopamine-mediated neuromodulation in prefrontal cortex of fragile X mice", J. Physiol., 591: 1133-1143 (2013).

Pilpel, Yair et al., "Synaptic ionotropic glutamate receptors and plasticity are developmentally altered in the CA1 field of Fmr1 knockout mice", J. Physiol., 587: 787-804 (2009).

Rogers, Tiffany D., "Reorganization of circuits underlying cerebellar modulation of prefrontal cortical dopamine in mouse models of autism spectrum disorder", Cerebellum, 12(4): 1-16 (2013).

Szekely, George A. et al., "Platelet Dopamine Uptake in Autistic and Other Psychotic Children, Inhibition by Imipramine", Prog. Neuro-Psychopharmacol, 4: 215-218 (1980).

Testa-Silva, Guilherme et al., "Hyperconnectivity and Slow Synapses during Early Development of Medial Prefrontal Cortex in a Mouse Model for Mental Retardation and Autism", Cereb. Cortex, 22(6): 1333-1342 (2012).

(56) References Cited

OTHER PUBLICATIONS

Wei, Hongen et al., "The Therapeutic effect of Memantine through the Stimulation of Synapse Formation and Dendritic Spine Maturation in Autism and Fragile X Syndrome", PLoS ONE, 7(5): e36981 (2012).

Weinshenker, David et al., "Fragile dopamine", Nature, 455: 607-608 (2008).

Xiao-Mian, Sun et al., "Study of 99mTc-TRODAT-1 imaging on human brain with children autism by single photon emission computed tomography", Proceedings of the 2005 IEEE, Engineering in Medicine and Biology 27th Annual Conference, Shanghai, China, Sep. 1-4, 2005.

\* cited by examiner

SYDNONIMINES-SPECIFIC DOPAMINE REUPTAKE INHIBITORS AND THEIR USE IN TREATING DOPAMINE RELATED DISORDERS

CROSS-REFERENCE TO RELATED APPLICATIONS

The present application is a divisional of U.S. patent application Ser. No. 13/180,996, filed Jul. 12, 2011, which issued as U.S. Pat. No. 8,415,385, which is a continuation of U.S. patent application Ser. No. 12/048,334, filed Mar. 14, 2008, which claims the benefit of U.S. Provisional Patent Application No. 60/894,739, filed Mar. 14, 2007, the entire disclosures of which are incorporated by reference herein.

GOVERNMENT RIGHTS STATEMENT

The invention described herein was made with funding provided by the U.S. National Institutes of Health, under Grant Nos. IR43DA013353-01, 2R44DA013353-02A1, 5R44DA013353-03, 2R44DA013353-04A1, 5R44DA013353-05 and 5R44DA013353-06. The Government has certain rights in this invention.

FIELD OF THE INVENTION

The present invention relates to certain Sydnonimine derivatives that bind specifically to dopamine transporter (DAT) proteins or the site of dopamine reuptake, compositions comprising same, and the use of such derivatives for treating, or delaying the progression of, various disorders and illnesses alleviated by inhibiting dopamine reuptake.

BACKGROUND OF THE INVENTION

Neurotransmitters are chemical "messengers" that function to relay electrical signals across the gap or synaptic cleft between one neuron, or nerve cell, and another. Neurotransmitters are stored in tiny sacs called vesicles, located at nerve endings. As an electrical signal arrives at a neuron's terminal, the vesicles move to the neural membrane and releases their neurotransmitter molecules into the synaptic cleft. The neurotransmitters formed in the pre-synaptic (or sending) neuron diffuse across the gap and lock onto binding sites or receptors on the membrane of a neighboring, post-synaptic (or receiving) neuron. Various biochemical processes are set into motion in the post-synaptic neuron when a neurotransmitter occupies a receptor on the surface thereof, including ion transport and release or inhibition of certain enzymes. The result is that a new electrical signal is generated in the post-synaptic neuron and the signal continues on.

Dopamine is a type of neurotransmitter that is formed in the brain and effects the processes that regulate movement, motivation, emotional response and the capacity to feel pleasure and pain. Dopamine is vital for performing balanced and controlled movements. After dopamine becomes bound to a receptor in the process of transmitting nerve signals, it is eventually released and removed from the synaptic cleft, back into the pre-synaptic neuron or glial cell by a reuptake process which operates under the influence of a protein, known as dopamine transporter (DAT), present on the neuron's outer membrane. In other words, the DAT protein acts to clear the dopamine out of the synaptic cleft, a process which is essential to normal transmission of nerve signals.

Furthermore, DAT protein is a major determinant of the intensity and duration of the dopaminergic signal. Knockout mice lacking the dopamine transporter (DAT-KO mice) display marked changes in dopamine homeostasis that result in elevated dopaminergic tone and pronounced locomotor hyperactivity (Gainetdinov et al. (2001) Proc. Natl. Acad. Sci., 98:11047-54; Hall et al. (2003) Neuropsychopharmacology, 28:620-8; Mateo et al. (2004) Proc. Natl. Acad. Sci., 101:372-7).

A number of behaviorial disorders and other debilitating illnesses can be alleviated by therapeutic agents that bind to DAT proteins and inhibit dopamine reuptake. These include cocaine addiction, attention deficit disorder, depression, Parkinson's disease, obesity narcolepsy, and schizophrenia, to name a few.

Cocaine addiction continues to be a major health care concern in the United States. According to a U.S. Department of Health and Human Services report (aspe.hhs gov/health/reports/cocaine/), there are over 2 million cocaine users in the United States. In an October 2002 report, the Drug Abuse Warning Network (DAWN) indicated that there were 638,484 emergency room (ER) visits in the U.S. in 2001 related to drug abuse, among which nearly one-third were due to cocaine.

Although research has shown that cocaine binds to various neurotransmitters in the brain, including not only dopamine, but serotonin and norepinephrine, as well, the reinforcing effect of cocaine, which is a factor in the addiction, is believed to be mediated by DAT protein binding, which causes inhibition of dopamine transport. One prominent behavioral effect of cocaine and other dopamine uptake inhibitors is the stimulation of locomotor activity. There is a significant correlation among affinities for [3H] WIN 35,428 (a DAT inhibitor) binding and potencies for stimulating activity for cocaine and structurally similar compounds compared with stimulation of mouse locomotor activity (Izenwasser et al. (2004) Eur. J. Pharmacol., 263:277-83; Kunko et al. (1998) Pharmacol. Exp. Ther., 285:277-84). There is ample evidence that attenuating dopamine receptor activity with receptor agonists or antagonists will affect patient behavior in addiction (Campiani et al. (2003) J. Med. Chem., 46:3822-39; Garcia-Ladona and Fox (2003) CNS Drug Rev., 9:141-58; Schlussman et al. (2003) Pharmacol. Biochem. Behav., 75:123-31; Platt et al. (2003) Psychopharmacology (Berl)., 166:298-305; Vorel et al. (2002) J. Neurosci., 22:9595-603; Ellinwood et al. (2002) Eur. Neuropsychopharmacol., 12:407-15).

It has been reported that dopamine transporter-selective compounds may be used alone or in combination with clinically available selective serotonin reuptake inhibitors (SSRIs) for treating cocaine abuse and addiction (Owens et al. (2002) Encephale., 28:350-5; Zhang et al. (2002) J. Med. Chem., 45:1930-41; Sanchez et al. (2003) Psychopharmacology (Berl), 167:353-62; Fish et al. (2004) J. Pharmacol. Exp. Ther., 308:474-80). Indeed, Sora et al. demonstrated the importance of the concurrent involvement of the dopamine transporter and serotonin transporter (SERT) proteins in the mechanism of dependency and addiction through evidence from neurotransmitter-transporter knockout models in mice (Sora et al. (2001) Proc. Natl. Acad. Sci., 98:5300-5). In this study, it was shown, with double knockout mice models of DAT and SERT, that mice with no dopamine transporter gene and either one copy or neither copy of the serotonin transporter displayed no preference for places where they had previously received cocaine. That is, without the concurrent reuptake of dopamine and serotonin, the mice are no longer "addicted" to cocaine. It is conceivable the dopamine and serotonin transport systems may have compensated for each other, and that cocaine dependency and reward behavior may be mediated through this redundancy or compensatory mechanism.

Because cocaine interacts with a number of neurotransport processes in the brain, as noted above, the discovery of a medication that is capable of antagonizing the effect of cocaine in clinical trials, without producing sedative or other undesirable side effects has proven to be a formidable task, and to date not successfully accomplished. Indeed, a number of clinically available medications approved for other therapeutic indications, especially reuptake/transporter blockers and/or receptor agonists, have been or are being tested in clinical trials for effectiveness in curtailing cocaine craving, dependency, and addiction; however, none has yet demonstrated long term efficacy.

Imbalances in the dopaminergic system have been implicated as contributing factors in the occurrence of several neuropsychiatric disorders, including attention deficit disorder, depression and certain symptoms of schizophrenia.

Attention deficit disorder is a learning disorder involving developmentally inappropriate inattention, with or without hyperactivity. The primary signs of attention deficit disorder are a patient's inattention and impulsivity. Inappropriate inattention causes increased rates of activity or reluctance to participate or respond. A patient suffering from attention deficit disorder exhibits a consistent pattern of inattention and/or hyperactivity-impulsivity that is more frequent and severe than is typically observed in individuals at a comparable level of development. Using positron emission tomography (PET) to study the dopamine levels in the brains of young human subjects, it was found that lower levels of brain dopamine may be a contributing factor for ADHD children (Volkow et al., *J. Neurosci.* 21(2) RC 121, (2001). Methylphenidate (Ritalin®), a compound of similar pharmacological profile to cocaine, specifically increases the brain dopamine level, hence exhibiting the phenotypic therapeutic effects.

The mechanism by which psychostimulants act as calming agents in the treatment of attention-deficit hyperactivity disorder (ADHD) or hyperkinetic disorder is currently unknown. Experiments have shown that mice lacking the gene encoding the DAT have elevated dopaminergic tone and exhibit marked hyperactive. This activity is exacerbated by exposure to a novel environment. Additionally, these mice were impaired in spatial cognitive function, and they showed a decrease in locomotion in response to psychostimulants. This paradoxical calming effect of psychostimulants depended on serotonergic neurotransmission. The parallels between DAT knockout mice and individuals with ADHD suggest that common mechanisms may underlie some of their behaviors and responses to psychostimulants. Haloperidol has been shown to produce a sedative effect on such mice.

Depression is one of the most common of emotional disorders, having a morbidity rate of over 10% in the general population. Depression is characterized by feelings of intense sadness, despair, mental slowing, loss of concentration, pessimistic worry, agitation, and self-deprecation (*Harrison's Principles of Internal Medicine*, 2490-2497 (Fauci et al., eds., 14$^{th}$ ed. 1998)). Depression can have physical manifestations including insomnia, hypersomnia, anorexia, weight loss, overeating, decreased energy, decreased libido, and disruption of normal circadian rhythms of activity, body temperature, and endosine functions. Moreover, as many as 10% to 15% of depressed individuals display suicidal behavior. R. J. Bladessarini, *Drugs and the Treatment of Psychiatric Disorders: Depression and Mania*, in Goodman and Gilman's *The Pharmacological Basis of Therapeutics*, 431 (9$^{th}$ ed. 1996). Strategies to increase synaptic concentrations of dopamine have been proposed as antidepressant therapies. (See e.g., D'Aquila et al., 2000, *Eur. J. Pharmacol.*, 405: 365-373).

Schizophrenia is considered by medical professionals to be a thought disorder, mood disorder and anxiety disorder. There is no known cure for schizophrenia. Thus, treatment is directed at the symptoms of schizophrenia and often involves administration of a combination of antipsychotic, antidepressant and antianxiety drugs. Antipsychotic drugs, such as haloperidol, have been in use for the treatment of schizophrenia since at least the 1950's. These established drugs act by blocking dopamine receptors and thereby control the hallucinations, delusions and confusion of schizophrenia. In the meantime, newer drugs have been introduced, e.g. quetiapine fumerate, and risperidone, which interact with both the dopamine and serotonin receptors, so as to treat the broad range of schizophrenia's symptoms.

One of the principal impediments to the success of treatments for schizophrenia is that patients frequently discontinue prescribed medication(s), especially those having undesirable side effects, such as blurred vision, dizziness, muscle spasms, cramps, tremors and other Parkinson-like symptoms.

The uncontrolled movements seen in sufferers of Parkinson's disease are due to the degeneration of dopamine neurons, loss of nerve terminals and consequent dopamine deficiency. Studies have shown that wild-type mice treated with a class of compounds called DAT blockers and genetic "DAT knock-out" mice are both resistant to the negative effects of specific neurotoxins, such as 1-methyl-4-phenyl-1,2,3,6-tetrahydropyridine (MPTP) and 6-hydroxydopamine (6-OHDA) on dopaminergic neurons. Therefore, a pharmacological blockade of DAT protein by potent and selective inhibitors may provide effective therapy by preventing the onset or delaying the progression of Parkinson's disease, and offer symptomatic benefits associated with increases in CNS dopamine levels.

Obesity is a disorder characterized by an abnormal increase of fat in the subcutaneous connective tissues. Among the therapeutic agents currently used to treat obesity are those that increase food intake, such as drugs that interfere with monoamine receptors, e.g., serotonin receptors, dopamine receptors, noradrenergic receptors and histamine receptors.

Narcolepsy is a neurological disorder marked by a sudden recurrent, uncontrollable compulsion to sleep, also associated with cataplexy (i.e., a sudden loss of muscle tone and paralysis of voluntary muscles associated with a strong emotion), sleep paralysis, hypnagogic hallucinations and automatic behaviors. The disease afflicts all races, females and males alike. It can vary in severity, with symptoms most commonly appearing in a person's teens and early twenties. Narcolepsy is clinically treated using central nervous system (CNS) stimulants, such as Ritalin® which exerts many of its effects through dopamine uptake blockade of central adrenergic neurons, and in particular by blocking DAT proteins.

Sydnocarb (3-(1-methyl-2-phenylethyl)-N-(phenylcarbomoyl)sydnone imine) has been discovered to have a CNS stimulatory effect, marked by an increase in locomotor activity with practically no peripheral sympathomimetic action, as described in GB Patent 1,262,830 and German Offenlegungsschrift 2028880. This discovery led to the synthesis of various sydnocarb analogues, which also act as CNS stimulants. See, for example, U.S. Pat. Nos. 4,277,609, 4,301,285, 4,371,697 and 4,446,322. However, sydnocarb, also known as mesocarb, and some of its closely related analogues are in fact derivatives of amphetamine, a highly addictive psycho-stimulant. When administered to human subjects, it is highly likely that individuals' metabolisms may convert sydnocarb back to amphetamine. Thus sydnocarb may exhibit higher abuse potential than those compounds that are without the propensity to be converted in this way. Indeed, sydnocarb is listed among the prohibited stimulants in the 2006 Guide to Prohibited Substances and Prohibited Methods of Doping, edition 6, Table 6, at 30, United States Anti-Doping Agency, Colorado Springs, Colo. (December 2005) (www.usantidoping.org).

Additionally, sydnocarb and closely related derivatives are modest reuptake inhibitors. Although having some preferential affinity towards dopamine reuptake proteins, these compounds exhibit affinity toward norepinephrine reuptake transporters, as well.

Because of the central and peripheral role played by the DAT in the dopaminergic system, it is an attractive target for therapeutic intervention against disorders and illnesses such as those described above that are alleviated by compounds that bind selectively to DAT and inhibit dopamine reuptake. Compounds that inhibit specific dopamine reuptake and lack central nervous system stimulating effects are inherently more valuable medications, as such agents would likely have fewer side effects in inducing medication dependency and drug abuse potential. Accordingly, there is an ongoing interest in the development of such compounds.

SUMMARY OF THE INVENTION

In brief, the present invention provides, in one aspect, a method for treatment of or delaying progression of disorders that are alleviated by inhibiting dopamine reuptake. The method involves administering to a patient in need of such treatment a therapeutically effective amount of a compound having the formula:

According to another aspect, the present invention provides novel Sydnonimine derivatives of the formula (I), above, with the proviso that the following known compounds are outside the scope of this aspect of the invention:
(i) N-phenylcarbamoyl-3-(benzyl)-sydnonimine;
(ii) N-(3',4'-dichlorophenyl)carbamoyl-3-phenethyl-sydnonimine;
(iii) N-(p-chlorophenyl)carbamoyl-3-phenethyl-sydnonimine; and
(iv) N-(m-trifluoromethyl)carbamoyl-3-phenethyl-sydnonimine.

In a further aspect, the present invention provides pharmaceutical compositions comprising one or more of the sydnonimine derivatives described herein in combination with a pharmaceutically acceptable carrier medium.

The DAT inhibitor compounds described herein differ from sydnocarb, not only in structure, but, more importantly, in their observed effects on animal behavior. Notably, sydnocarb is a stimulant, as evidenced by its locomotor stimulating effect in open field studies. J. Witkin et al., J. Pharm. Exptl. Therap., 288(3): 1298-1310 (1999). By contrast, the same animal model study, also conducted NIDA, has shown that the compounds of the present invention have the effect of suppressing locomotor activity in a dose dependent manner. It is expected that the central dopaminergic effect of these compounds, without central nervous system stimulation, will lead to a myriad of therapeutic applications for which sydnocarb would be ineffective. Moreover, unlike syndocarb and its previously known analogues, the compounds of the present invention are potent and specific dopamine reuptake inhibitors, having no appreciable affinity towards norepinephrine reuptake proteins. Another advantage of the compounds described herein is that they exhibit no propensity for conversion to amphetamine in vivo.

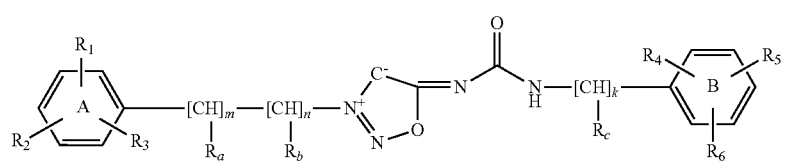

(I)

Figure 1A:
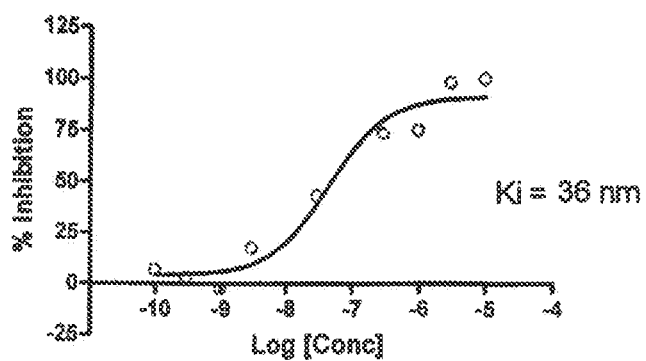
FIG. 1 is a graphical representation of the $IC_{50}/K_i$ profile of representative examples of sydnonimine derivatives used
Figure 1B:
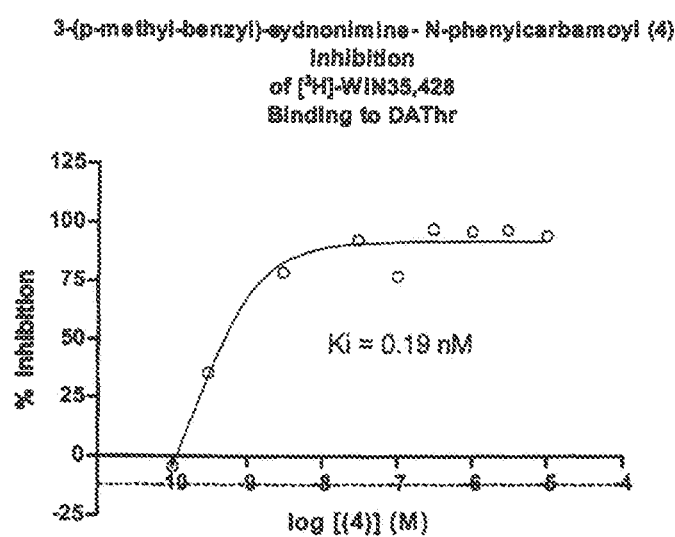
Figure 1C:
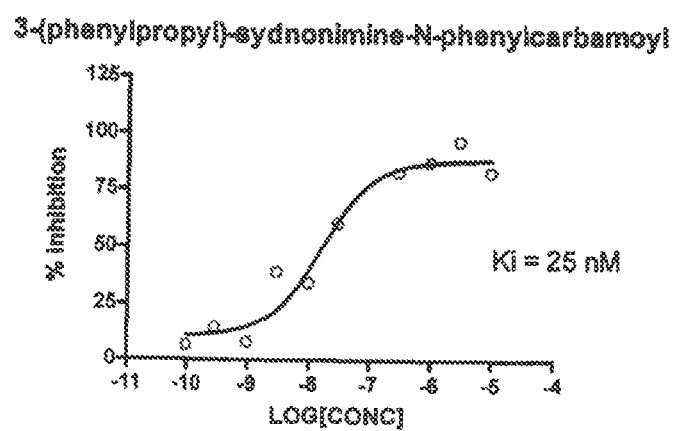
Figure 1D:
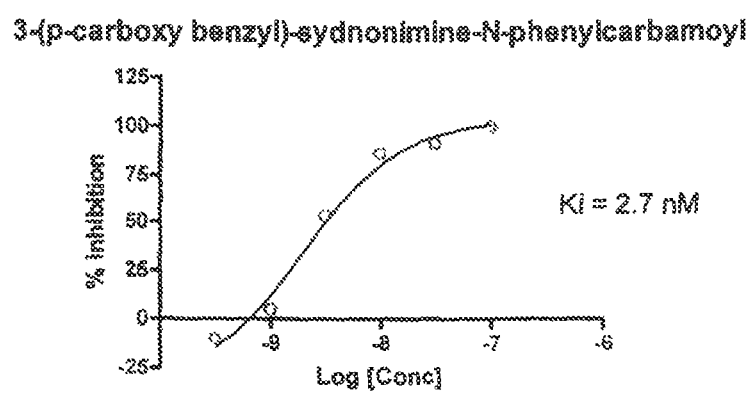
Figure 1E:
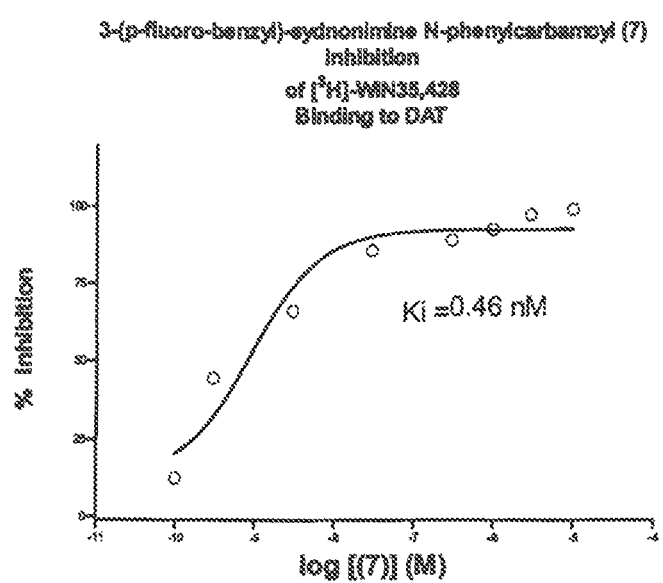
Figure 1F:
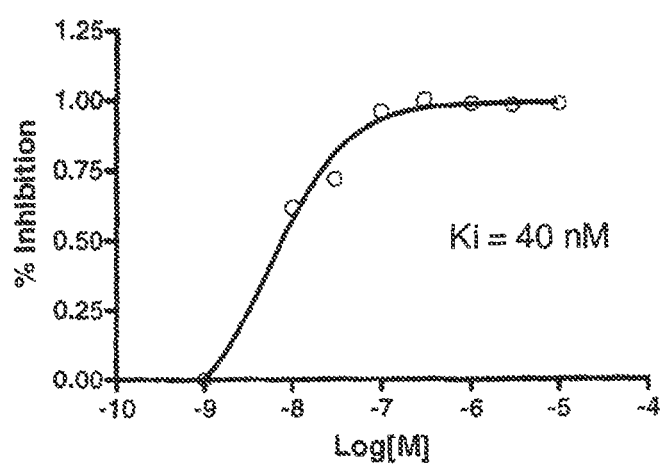
Figure 1G:
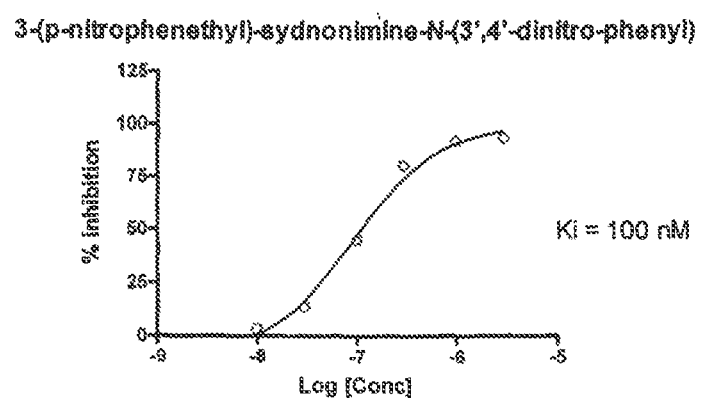
Figure 2A:
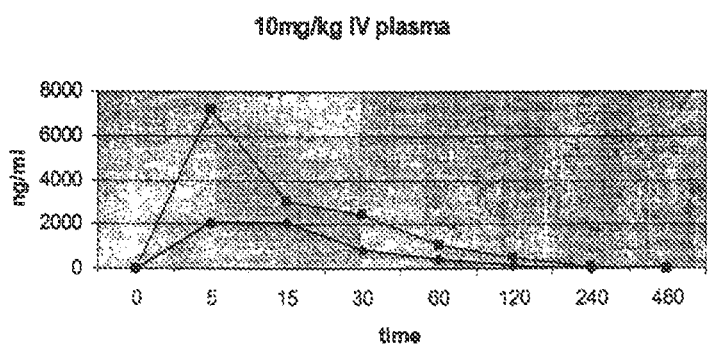
Figure 2B:
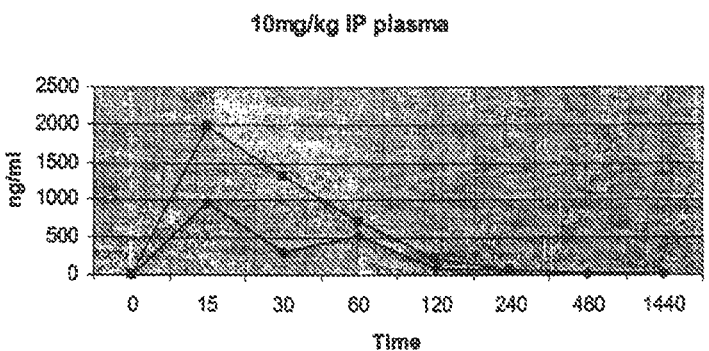
Figure 2C:
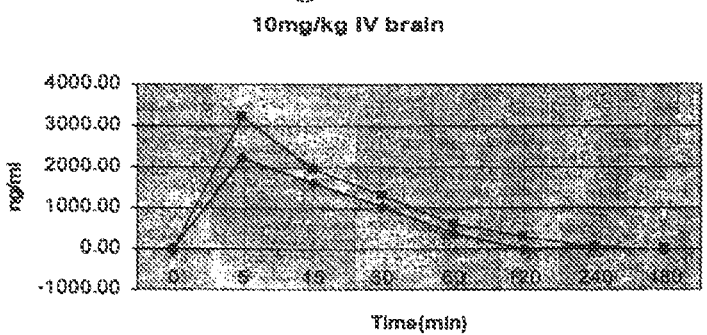
Figure 2D:
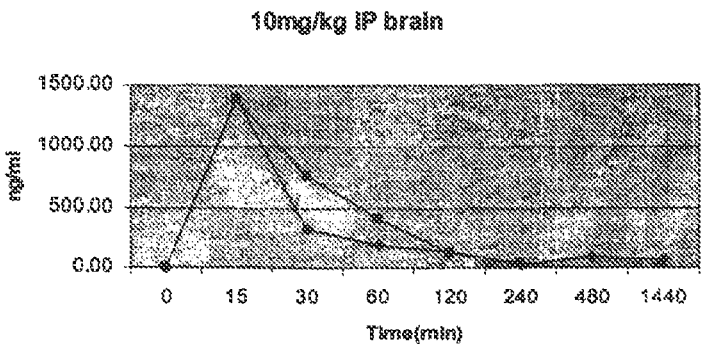

wherein $R_1$, $R_2$, $R_3$, $R_4$, $R_5$ and $R_6$, independently of one another, are radicals selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl;

Ra, Rb and Rc, independently of one another, represent radicals selected from H, $C_1$-$C_4$ alkyl, phenyl or phenyl $C_1$-$C_4$ alkyl;

m, n and k are independent integers from 0-4, except that m+n≠0, and Rb≠alkyl when m+n=2; and the pharmaceutically acceptable salts of said compound.

in the practice of this invention, namely, FIG. 1A is 3-(benzyl)-sydnonimine-N-phenylcarbamoyl; FIG. 1B is 3-(p-methyl-benzyl)-sydnonimine-N-phenylcarbamoyl; FIG. 1C is 3-(phenylpropyl)-sydnonimine-N-phenylcarbamoyl; FIG. 1D is 3-(p-carboxyl benzyl)-sydnonimine N-phenylcarbamoyl); FIG. 1E is 3-(p-fluoro-benzyl)-sydnonimine N-phenylcarbamoyl; FIG. 1F is 3-phenethyl-sydnonimine-N-(3'-4'-dichloro-phenyl)carbamoyl and FIG. 1G is 3-(p-nitrophenethyl)-sydnonimine-N-(3',4'-dinitro-phenyl) carbamoyl.

FIGS. 2A-2D are graphs of a pharmacokinetic profile comparison showing that the compound of Example 6 (see below; -■-), exhibits slightly higher bioavailablilty than the compound of Example 3 (-♦-) at the same dosage using different routes of administration.

Figure 3:
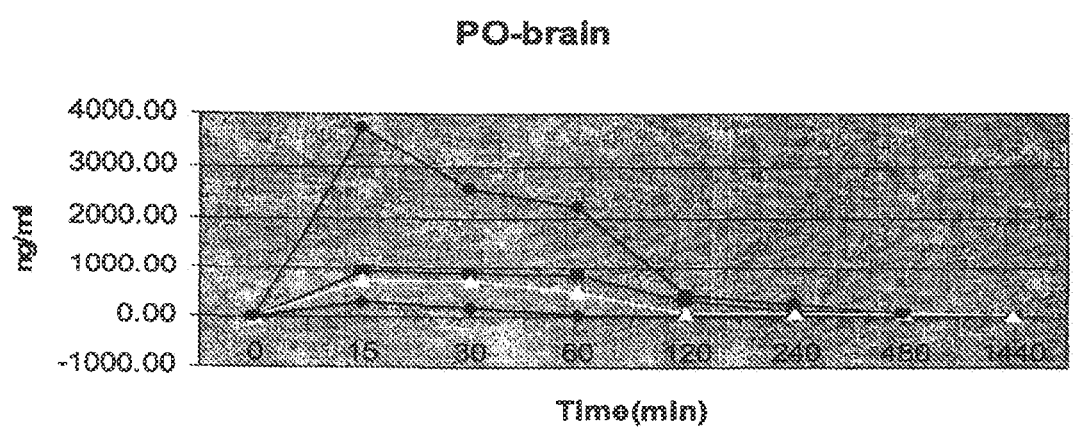

FIG. 3 is a graph of a pharmacokinetic profile comparison showing that the compound of Example 6 (-■-=10 mg/kg;

-●-=30 mg/kg) demonstrates better oral bioavailabilty than the compound of Example 3 (-♦-=10 mg/kg; -Δ-=30 mg/kg) at different dosages.

Figure 4A:
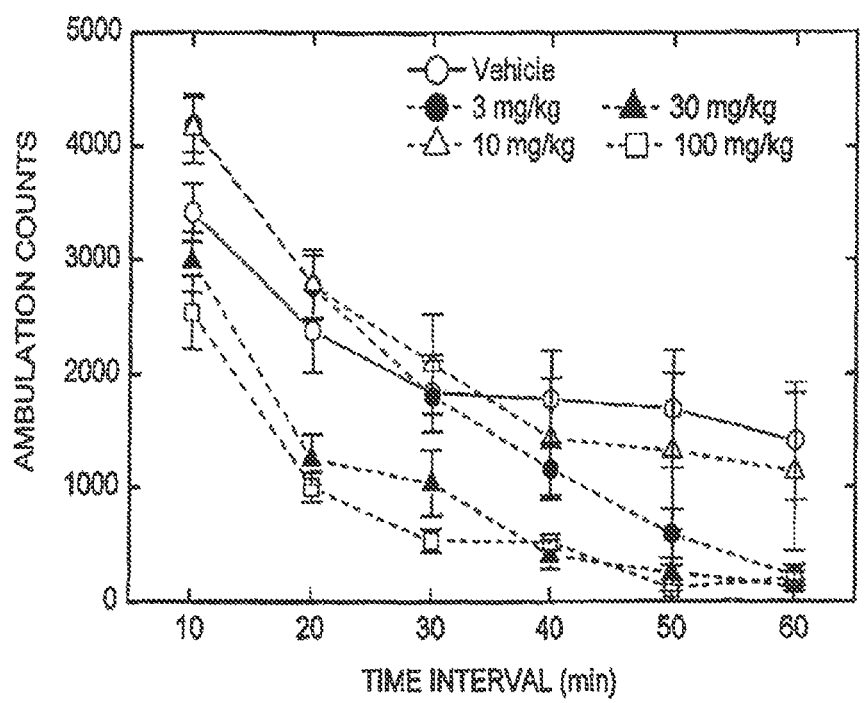
Figure 4B:
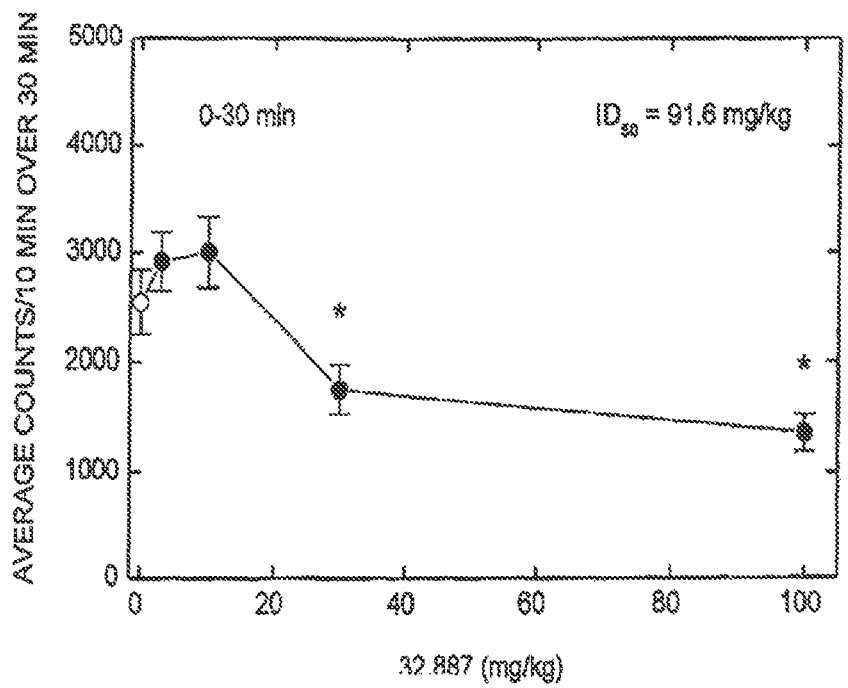

FIGS. 4A and 4B are graphs showing that the compound of Example 3 demonstrates a dose dependent suppression of spontaneous locomotor activity (NIDA).

Figure 5A:
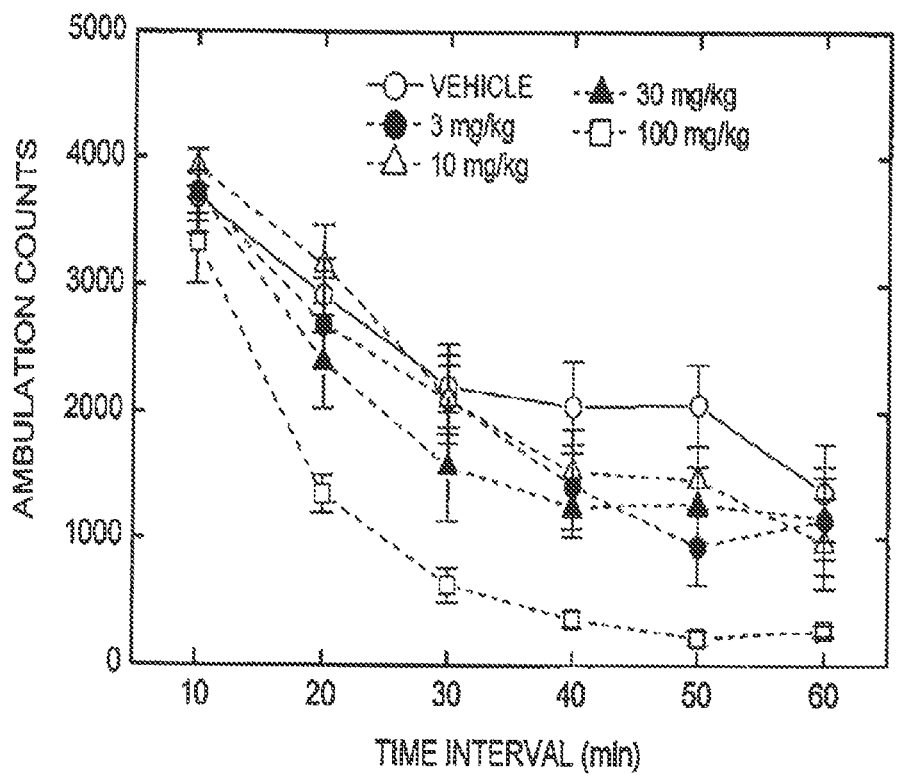
Figure 5B:
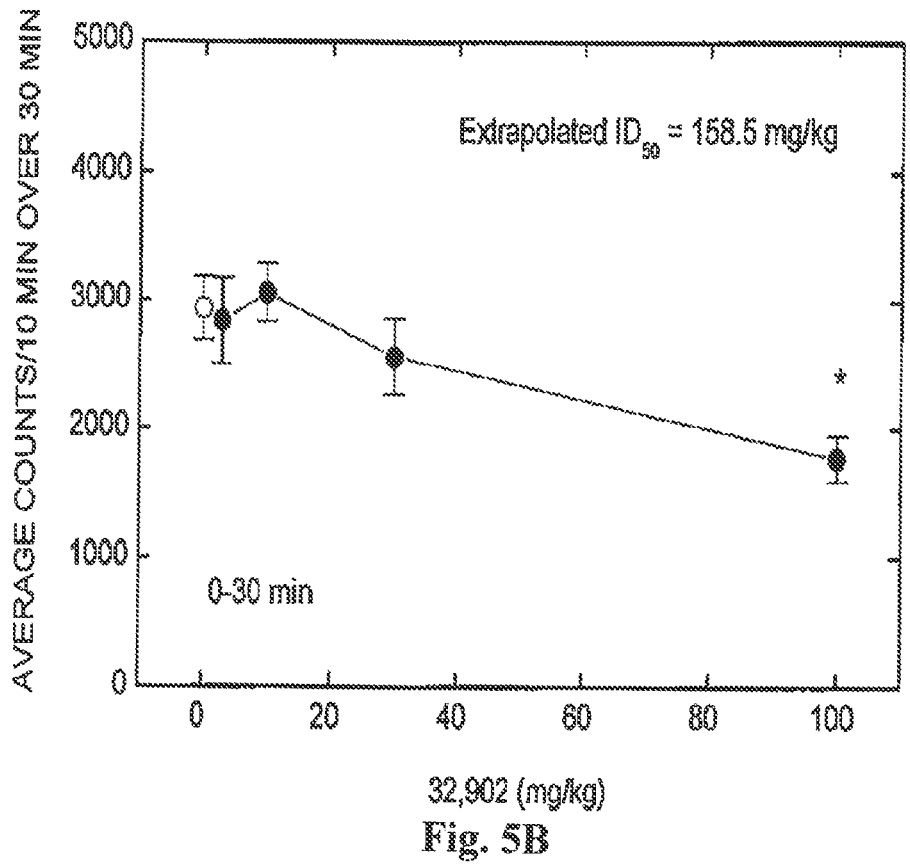

FIGS. 5A and 5B are graphs showing that the compound of Example 6 demonstrates a dose dependent suppression of spontaneous locomotor activity (NIDA).

Figure 6A:
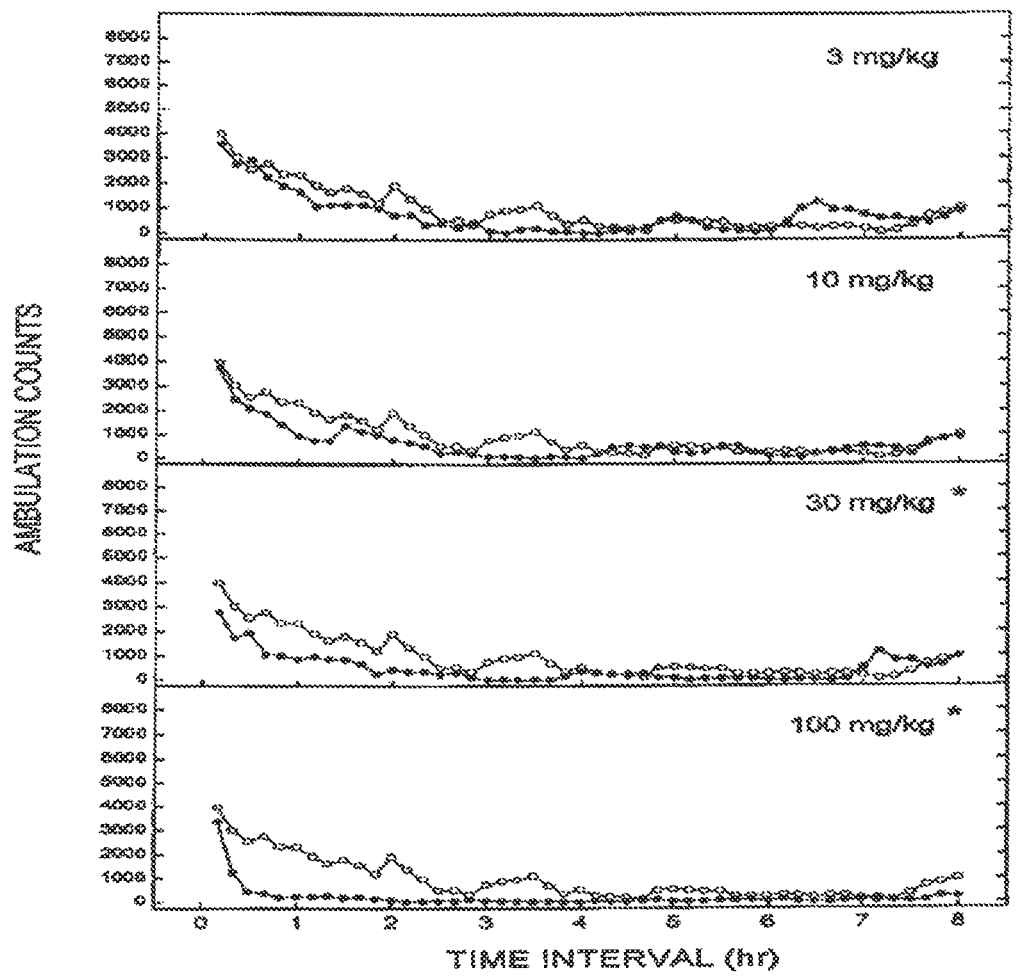
Figure 6B:
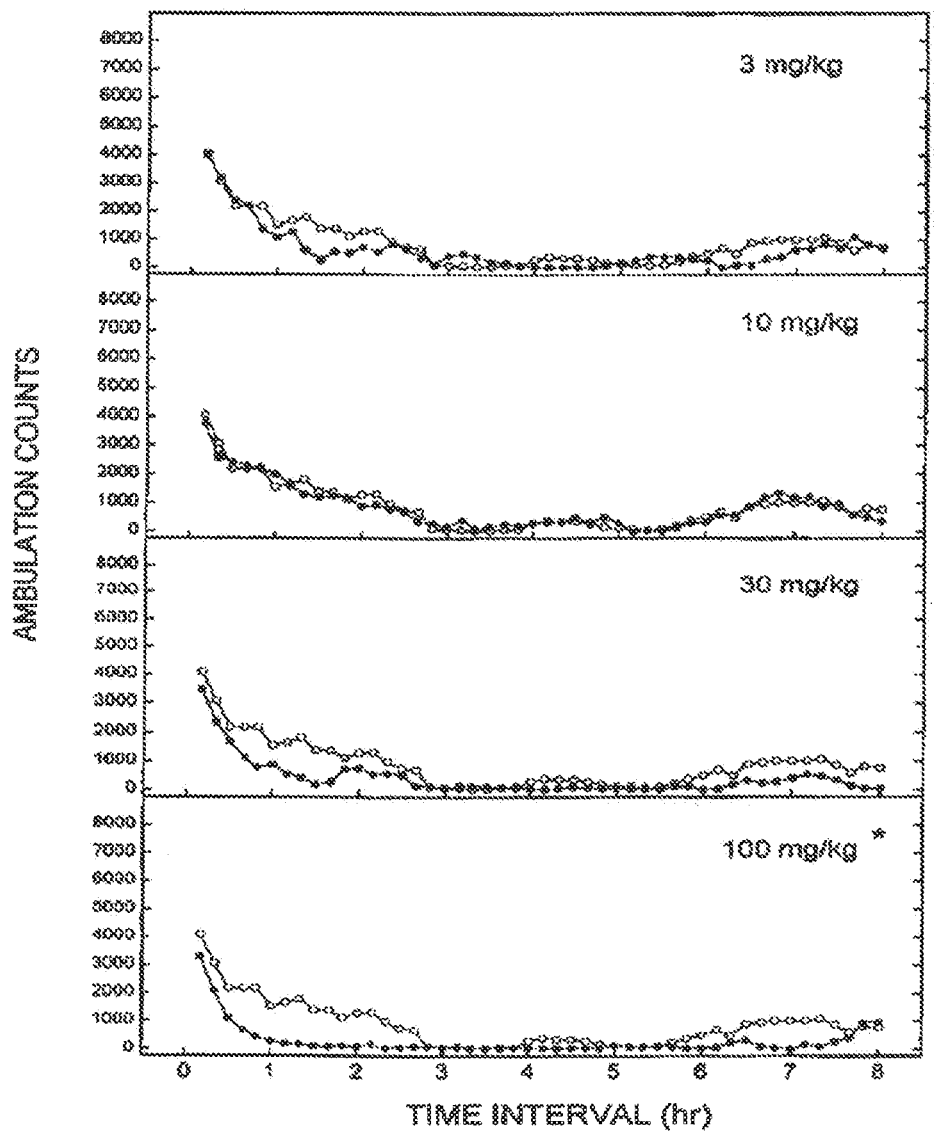

FIGS. 6A and 6B are graphical representations of test results demonstrating that the compound of Example 3 and the compound of Example 6, respectively, are capable of suppressing spontaneous locomotor activity for at least 3 hours (-●-=DAT inhibitor and -○-=vehicle in FIGS. 6A and 6B).

Figure 7A:
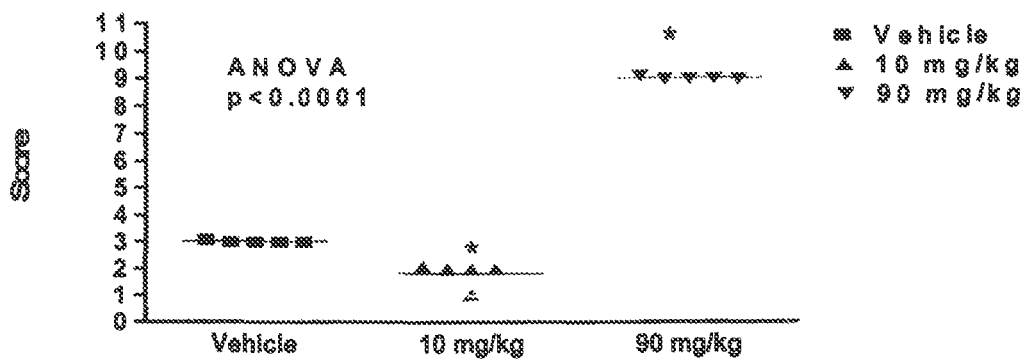
Figure 7B:
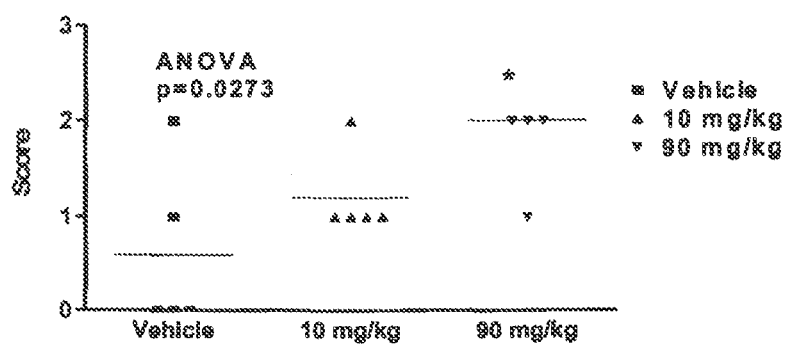
Figure 7C:
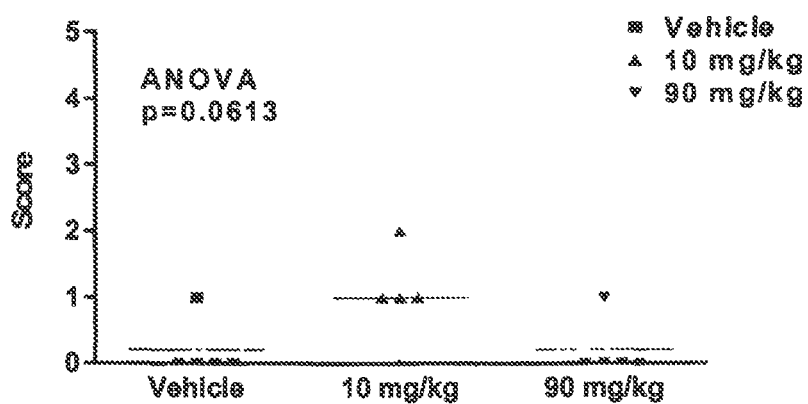

FIGS. 7A-7C are a series of graphs showing that the compound of Example 3 induces significant behavioral effects in an Irwin Behavioral Battery (FIG. 7A: Spontaneous activity; FIG. 7B: Grip strength; FIG. 7C: Limb tone).

Figure 8:
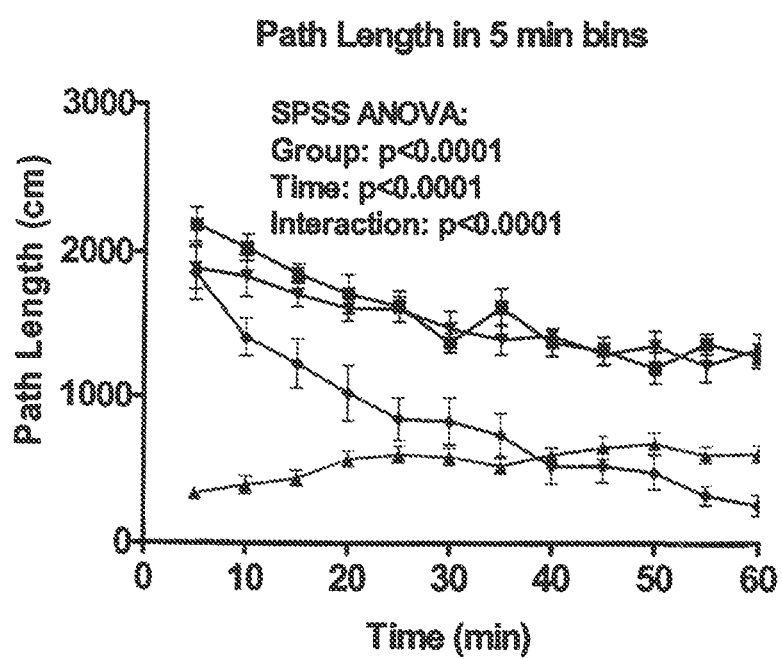
Figure 9A:
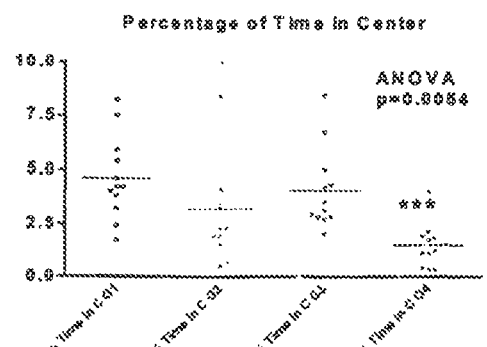
Figure 9B:
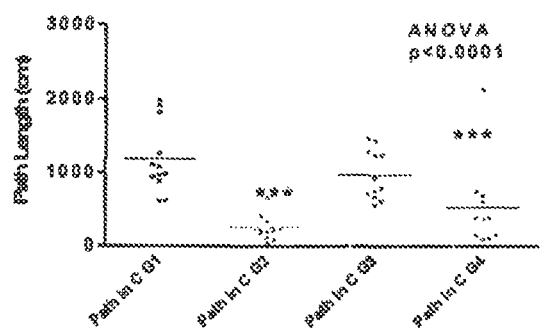
Figure 9C:
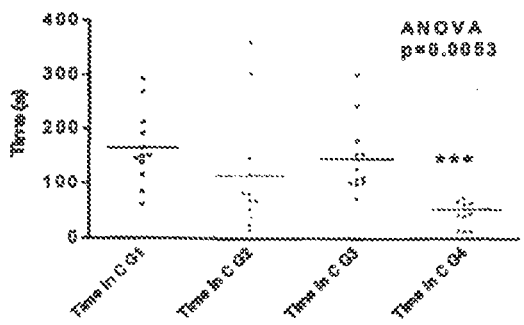
Figure 9D:
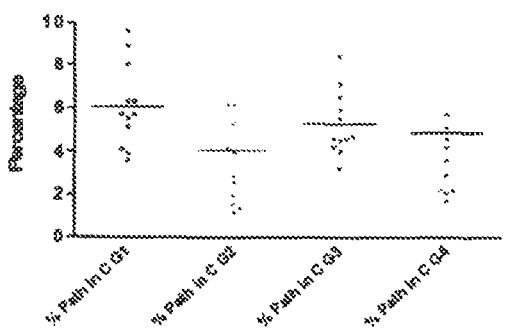

FIG. 8 is a graph showing that the compound of Example 3 reduces locomotor activity in Open Field testing (-■-=vehicle; -▼-=test compound, 10 mg/kg; -♦-=test compound, 90 mg/kg; -▲-=buspirone, 6 mg/kg).

FIGS. 9A-9D are a series of graphs showing that the compound of Example 6 induces anxiolytic effects in Open Field testing (-■-=vehicle; -Δ-=buspirone, 6 mg/kg; -▼-=test compound, 10 mg/kg; -✕-=test compound, 90 mg/kg).

Figure 10:
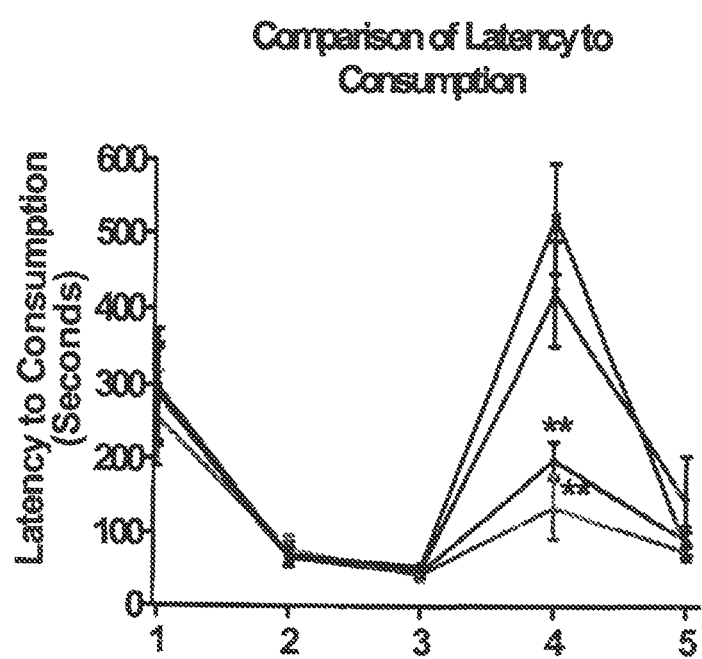

FIG. 10 is a graph showing that the compound of Example 3 induces an anxiolytic effect in novel environment-induced feeding suppression (-■-=vehicle; -●-=buspirone, 6 mg/kg; -▼-=test compound, 10 mg/kg; -♦-=test compound, Ex. 3, 90 mg/kg)

Figure 11:
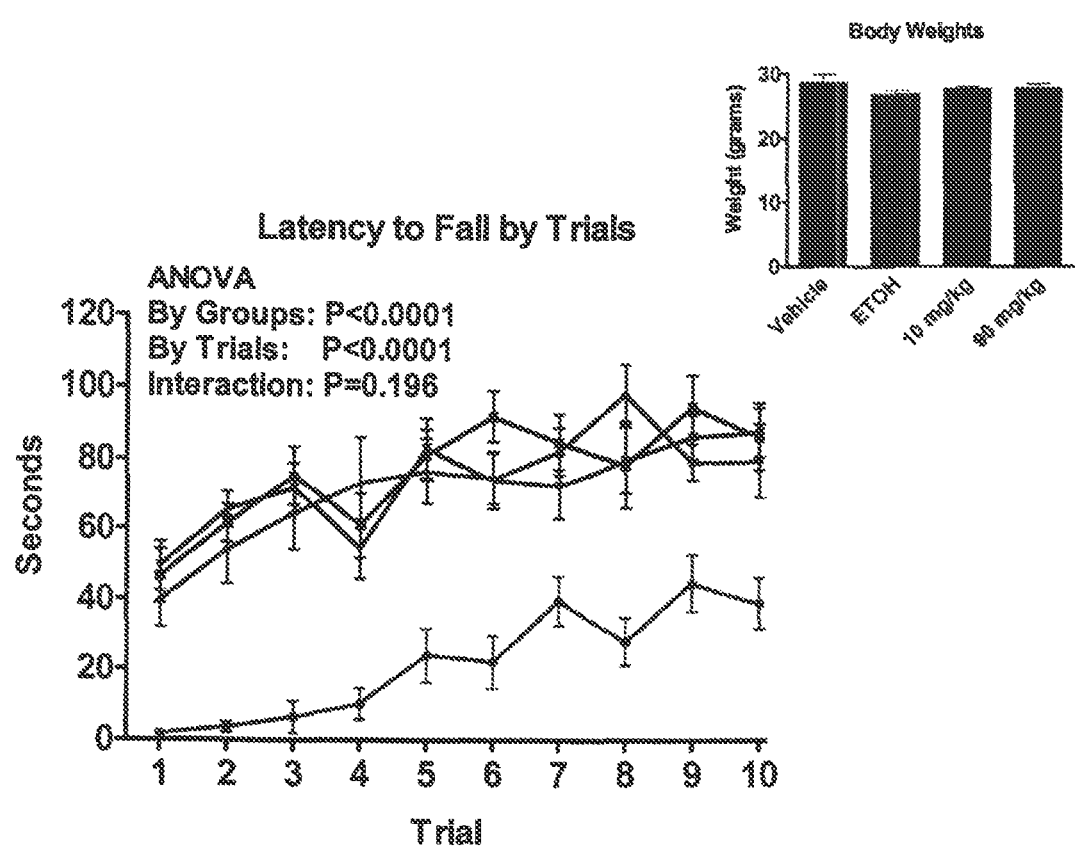

FIG. 11 is a graph showing that the compound of Example 3 did not affect Rotarod Performance (-■-=vehicle; -●-=EtOH; -▼-=Ex. 3, 10 mg/kg; -♦-=Ex. 3, 90 mg/kg).

DETAILED DESCRIPTION OF THE INVENTION

As previously noted, the present invention includes compounds of Formula I, above, pharmaceutical compositions comprising such compounds and methods of using such compounds for treating various disorders and illnesses alleviated by inhibiting dopamine reuptake, or preventing or delaying the progression of those disorders and illnesses.

It should be appreciated that compounds of Formula I, above, may have one or more asymmetric centers and thus exist as stereoisomers, including enantiomers and diastereomers, which are usually named according to the Cahn-Ingold-Prelog system. Although the structure of Formula I is represented without regard to stereochemistry, it is intended to include all possible stereoisomers, which may be racemic mixtures or other mixtures of R and S stereoisomers (scalemic mixtures which are mixtures of unequal amounts of enantiomers), as well as resolved, substantially pure optically active forms, and pharmaceutically acceptable salts thereof.

Stereoisomers of the compounds of formula (I), above, can be selectively synthesized or separated into pure, optically-active form using conventional procedures known to those skilled in the art of organic synthesis. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

All of the various isomeric forms of the compound of Formula I, above, are within the scope of this invention.

As used herein, the "alkyl" refers to saturated straight and branched chain hydrocarbon radicals, having 1-6 and preferably 1-4 carbon atoms. The term "alkenyl" is used to refer to unsaturated straight and branched chain hydrocarbon radicals including at least one double bond, and having 2-7 and preferably 2-5 carbon atoms. Such alkenyl radicals may be in trans(E) or cis(Z) structural configurations. The term "alkynyl" is used herein to refer to both straight and branched unsaturated hydrocarbon radicals including at least one triple bond and having 2-7 and preferably 2-5 carbon atoms.

The term "cycloalkyl" as used herein refers to a saturated cyclic hydrocarbon radical with one or more rings, having 3-14 and preferably 5 or 6-10 carbon ring-atoms.

Any alkyl, alkenyl, alkynyl or cycloalkyl moiety of a compound described herein may be substituted with one or more groups, such as halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy.

The term "aryl" as used herein refers to an aromatic hydrocarbon radical composed of one or more rings and having 5 or 6-14 carbon atoms and preferably 5 or 6-10 carbon atoms, such as phenyl, naphtnyl, biphenyl, fluorenyl, indanyl, or the like. Any aryl moiety of a compound described herein may be substituted with one or more groups, such as halogen, OH, SH, $NH_2$, $C_1$-$C_4$ monoalkylamino, $C_1$-$C_4$ dialkylamino, COOH, CN, $NO_2$, C1-C4 alkyl or C1-C4 alkoxy. The aryl moiety is preferably substituted or unsubstituted phenyl.

The term "arylalkyl" or "aralkyl" as used herein refers to radicals having 6 to 20 carbon atoms that combine both an aryl and an alkyl group, as defined above. Any aralkyl moiety of a compound described herein may optionally be substituted with one or more of the same substituent groups mentioned above in reference to the aryl radical.

The term "halogen" or "halo" as used herein refers to Fl, Cl, Br and I.

The term "alkoxy" refers to alkyl-O—, in which alkyl is as defined above.

The term "alkylthio" refers to alkyl-S—, in which alkyl is as defined above.

The term "carboxy" refers to the moiety —C(═O)OH.

The term "carbalkoxy" refers to the moiety —C(═O)O-alkyl, in which alkyl is as defined above.

The term "carboxamido" refers to the moiety —C(═O) O—NR'R", in which R' and R", each independently represents H, alkyl, aryl or aralkyl, all as previously defined.

The term "alkylsulfonyl" refers to the moiety —S(═O)$_2$-alkyl, in which alkyl is as previously defined.

The term "alkylsulfonyloxy" refers to the moiety —OS(═O)$_2$-alkyl, wherein alkyl is as previously defined.

The term "amino(monoalkylamino-, dialkylamino-)sulfinyl" refers to the moiety —S(═O)NR'R" in which R' and R" each independently represents H, alkyl, aryl or aralkyl, all as previously defined.

The term "amino(monoalkylamino-, dialkylamino-)sulfonyl" refers to the moiety —S(═O)$_2$NR'R", in which R' and R" each independently represents H, alkyl, aryl or aralkyl, all as previously defined.

The term "alkylsulfonylamino" refers to the moiety —NHS(═O)$_2$-alkyl, in which alkyl is as previously defined.

The term "hydroxysulfonyloxy" refers to the moiety —OS(=O)₂OH.

The term "alkoyxsulfonyloxy" refers to the moiety —OS(=O)₂O-alkyl, in which alkyl is as previously defined.

The term "alkylsulfonyloxy" refers to the moiety —OS(=O)₂-alkyl, in which alkyl is as previously defined.

The term "hydroxysulfonyl" refers to the moiety —S(=O)₂OH.

The term "alkoxysulfonyl" refers to the moiety —S(=O)₂O-alkyl, wherein alkyl is as previously defined.

The term "alkylsulfonylalkyl" refers to the moiety -alkyl-S(=O)₂-alkyl, wherein alkyl (each instance) is as previously defined.

The term "amino(monoalkylamino-, dialkylamino-)sulfonylalkyl" refers to the moieties -alkyl-S(=O)₂—NR'R", wherein alkyl is as previously defined, and R' and R" each independently represents H, alkyl, aryl or aralkyl, all as previously defined.

The term "amino(monoalkylamino-, dialkylamino-)sulfinylalkyl" refer to the moieties -alkyl-S(=O)—NR'R", wherein alkyl is as previously defined, and R' and R" each independently represents H, alkyl, aryl or aralkyl, all as previously defined.

Preferred are the compounds of Formula I, above, wherein phenyl rings A and/or B are mono- or di-substituted. When the A and/or B ring is mono-substituted, para-substitution is preferred. When the A and/or B ring is di-substituted, 3,4 di-substitution is preferred. Most preferred are compounds in which the A ring is para-substituted, e.g., N-phenylcarbamoyl-3-(p-methyl-benzyl)sydnominine, compounds in which the B ring is 3,4-di-substituted, e.g., N-(3',4'-dichlorophenyl)carbamoyl3-phenethyl-sydnominine and compounds in which the A ring is para-substituted and the B ring is 3,4-di-substituted, e.g., N-(3',4'-dinitrophenyl)carbamoyl-3-(p-nitrophenethyl)-sydnominine.

The term "pharmaceutically acceptable salts" as used herein refers to salts derived from non-toxic physiologically compatible acids and bases, which may be either inorganic or organic. Thus, when a compound of Formula I has an acid moiety, e.g., 3-(p-carboxylbenzyl), sydnominine-N-phenyl-carbamoyl, useful salts may be formed from physiologically compatible organic and inorganic bases, including, without limitation, alkali and alkaline earth metal salts, e.g., Na, Li, K, Ca, Mg, as well as ammonium salts, and salts of organic amines, e.g., ammonium, trimethylammonium, diethylammonium, and tris-(hydroxymethyl)methylammonium salts. The compounds of the invention also form salts with organic and inorganic acids, including, without limitation, acetic, ascorbic, lactic, citric, tartaric, succinic, fumaric, maleic, malonic, mandelic, malic, phthalic, salicyclic, hydrochloric, hydrobromic, phosphoric, nitric, sulfuric, methane sulfonic, naphthalene sulfonic, benzene sulfonic, toluene sulfonic and similar known, physiologically compatible acids. In addition, when a compound of Formula I contains both a basic moiety and an acidic moiety, zwitterions ("inner salts") may be formed and are included within the term "salt(s)" as used herein.

The sydnominine derivatives described herein, including the pharmaceutically acceptable salts thereof, can be conveniently prepared by those having ordinary skill and experience in organic synthesis, using known starting materials, and following the general synthetic scheme shown below, in which the radicals R₁-R₆ are as previously defined:

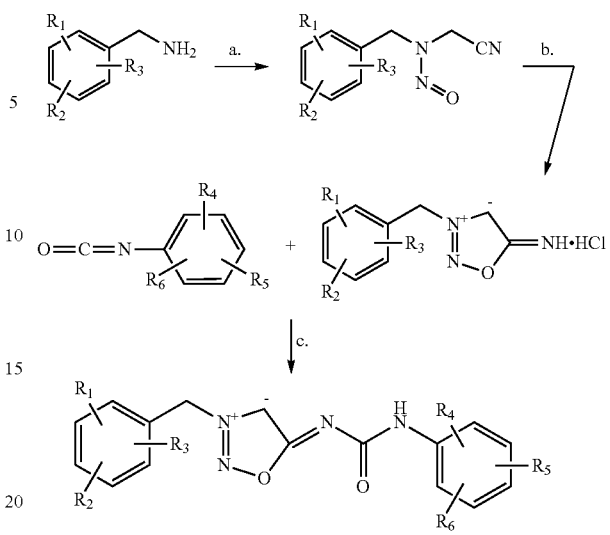

a. HCHO, NaNO₂, KCN; b. HCl; c. NaHCO₃

Chemical reactions for the preparation of specific sydnominine derivatives which may be used in the practice of this invention are described in further detail hereinbelow. The starting materials for these reactions are available from commercial sources. See also, U.S. Pat. No. 3,277,108.

In vitro studies have been performed that demonstrate the specific DAT inhibition activity of the compounds of the invention. DAT inhibition activity was tested according to the procedure described by J. Javitz et al., Mol. Pharmacol., 26: 35-44 (1984). The test results for a number of representative compounds of the invention are reported hereinbelow.

As used herein, the expression "method of treating disease alleviated by inhibiting DAT" refers to a treatment using one or more of the compounds described above, which provides relief either by freeing the recipient of a disease or condition mediated by DAT or easing the symptoms or effects of such disease or condition. The method of the invention is intended for treating, preventing, managing and/or delaying the progression of the following: pulmonary conditions such as lung edema; ischemia-reperfusion injury; cardiac conditions, such as acute decompensated heart failure and the cardiorenal syndrome; hyperprolactinaemia (BrE), hyperprolactinemia (AmE) and microprolactinoma; pain including chronic or neuropathic pain; catatonic, dyskinesia, restles legs syndrome and related movement disorders; stress, chronic posttraumatic stress disorder, anxiety disorders, obsessive-compulsive disorders, postpartum depression; schizophrenia, manic, bipolar, and affective disorder; executive function disorders, such as ADHD, Tourette syndrome and autism; cocaine, amphetamine, alcohol dependency, and addictive behavior, such as pathological gambling; neuroendocrine regulatory disorders; inflammatory conditions, autoimmune diseases and rheumatism; neoplastic disorders, such as pituitary carcinomas, macroprolactinomas; visual sensory disorders, color deficiency; and ejaculatory and related sexual dysfunction. The diseases and conditions enumerated above are given by way of example and not by way of limitation.

In general, the compounds of the invention can be administered to achieve specific dopamine reuptake inhibition by using any acceptable means known in the art, either alone or in combination with one or more other therapeutic agent. Thus, the active agent(s) can be administered enterally, parenterally, such as by intravenous infusion, intramuscular, intraperitoneal or subcutaneous injection, by liposome-mediated delivery, vaginally, by inhalation or insufflation, transdermally or by otic delivery.

Normally, a daily dose of the compound of the invention in the range from about 0.01 mg to about 200 mg/kg of body weight can be administered. A daily dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the gender, age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds of the invention will typically be administered from 1-4 times a day, so as to deliver the above-mentioned daily dosage. However, the exact regimen for administration of the compounds and compositions described herein will necessarily be dependent on the needs of the individual subject being treated, the type of treatment administered and the judgment of the attending medical specialist. As used herein, the term "subject" includes both humans and animals.

The compounds of the invention may be administered as such, or in a form from which the active agent can be derived, such as a prodrug. A prodrug is a derivative of a compound described herein, the pharmacologic action of which results from the conversion by chemical or metabolic processes in vivo to the active compound. Prodrugs include, without limitation, ester derivatives of the compounds of formula I, above. Other prodrugs may be prepared according to procedures well known in the field of medicinal chemistry and pharmaceutical formulation science. See, e.g., Lombaert et al., J. Med. Chem., 37: 498-511 (1994); and Vepsalainen, Tet. Letters, 40: 8491-8493 (1999).

The DAT specific compounds described herein and the pharmaceutically acceptable salts thereof are preferably formulated in unit dosage form for ease of administration and uniformity of dosage. The expression "unit dosage form" as used herein refers to a physically discrete unit of the active agent appropriate for the subject to be treated. Each dose should contain the quantity of active ingredient calculated to produce the desired therapeutic effect, either as such, or in association with the selected pharmaceutical carrier medium and/or supplemental active agent(s), if any. Typically, the DAT inhibitory compounds of the invention will be administered in dosage form containing from about 0.01 mg to about 200 mg of the active ingredient, with a range of about 30 mg to about 100 mg being preferred.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

A pharmaceutical composition in accordance with the present invention comprises one or more of the compounds of Formula I, above, in combination or admixture with a pharmaceutically acceptable carrier medium. The composition may, if desired, be administered in conjunction with one or more supplemental active agents. For example, the DAT inhibiting agent may be used in combination with L-dopa for the treatment of Parkinson's disease; or in combination with a selective serotonin reuptake inhibitor (SSRI) for the treatment of depression and or cocaine abuse and addiction; or in combination with dopamine D2 antagonist for the treatment of schizophrenia; or in combination with cholinergic modulators for the treatment of Alzheimer disease or other diseases or conditions in which patients have a cognitive deficit. The compound(s) of the invention may be administered either simultaneously (e.g., in the same formulation or not) or sequentially with the supplemental therapeutic agent(s).

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, $20^{th}$ edition, A. R. Genaro et al., Part 5, Pharmaceutical Manufacturing, pp. 669-1015 (Lippincott Williams & Wilkins, Baltimore, Md./Philadelphia, Pa. (2000)) discloses various carriers used in formulating pharmaceutical compositions and known techniques for the preparation thereof. Except insofar as any conventional pharmaceutical carrier medium is incompatible with the DAT inhibitor compounds of the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further provides controlled-release or sustained-release therapeutic dosage forms for the pharmaceutical composition, in which the composition is incorporated into a delivery system. This dosage form controls release of the active agent(s) in such a manner that an effective concentration of the active agent(s) in the bloodstream can be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In the pharmaceutical compositions of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

While not wishing to be confined to any particular theory as to the biochemical mechanism of action of the compounds described herein, considering that these compounds have shown 1) highly potent and specific interaction with dopamine reuptake proteins, 2) fast onsite absorption and distribution (e.g. brain), and 3) little interaction with other proteins including the most prevalent metabolic enzymes, it is believed that these compounds may be used 1) alone to ameliorate disease conditions, central and or peripheral, when endogenous dopaminergic functions are augmented by the inhibition of dopamine reuptake; 2) in combination with dopamine (or dopaminergic agonists) to provide synergistic effects of augmented endogenous dopaminergic functions and drug effects; and 3) in combination with other than dopaminergic mechanism medications, when the treatment of disease requires the consideration of complex and multifaceted disease etiology.

The following examples are provided to describe the invention in further detail. These examples are provided for illustrative purposes only and are not intended to limit the invention in any way.

EXAMPLE 1

Preparation of
N-phenylcarbamoyl-3-(benzyl)-sydonimine 1.2 ml 7.5N aq. HCl was stirred (at 0° C.) into a mixture of 0.94 g benzyl amine and 0.58 g of potassium cyanide in 2 ml of water. 0.7 g formaldehyde was then added dropwise into the mixture. The resulting mixture was stirred at room temperature for 2 hours and then cooled to 0° C. A solution of 0.62 g sodium nitrite in 1 ml water was added slowly dropwise to the mixture followed by the addition of 1.2 ml7.5N HCl aq. solution while cooling. The mixture was stirred at room temperature for 1 hour. Ether was used to extract the resulting mixture three times. The combined ether solution was dried with anhydrous sodium sulfate. The solvent was removed under reduced pressure. N-nitrosobenzylaminoacetonitrile (see reaction scheme) was obtained as a yellow oil. The nitroso intermediate was then treated with 500 ml HCl ethereal solution (2.0 M) and stirred for 30 minutes at room temperature. White precipitate was obtained and recrystallized with 2-propanol, resulting in a white crystal. 2.84 g of the 3-benzyl-sydonimine hydrochloride thus produced was dissolved in 25 ml of water. To the solution was added 1.34 g sodium bicarbonate at 0° C. 2.45 ml of phenyl isocyanate was then added dropwise to the mixture and stirred at 0° C. for 4 hours to the resulting mixture was added 10 ml of ether to help the yellow crystal precipitate. Methanol was used as solvent for recrystallization. The desired product was obtained as yellow crystal.

EXAMPLES 2-7

The compounds N-phenylcarbamoyl-3-(p-carboxylbenzyl-sydonimine (2); N-phenylcarbamoyl-3-(p-methyl-benzyl)-sydonimine (3); N-(3',4'-dichlorophenyl) carbamoyl-3-phenethyl sydonimine (4); N-(3',4'-dinitrophenyl) carbamoyl-3-p-nitrophenethyl sydonimine (5); N-phenylcarbamoyl-3-(phenylpropyl)-sydnonimine (6); and N-phenylcarbamoyl-3-(p-fluoro-benzyl)-sydnonimine (7) were synthesized following essentially the same procedure as described in Example 1, above, with appropriate substitution of different starting materials in equivalent amounts.

EXAMPLE 8

I. Dopamine Transporter Binding Assay [3H]WIN 35,428
  This assay was carried out according to the procedure described by Javitch, J. J. et al., Mol. Pharmacol. 26: 35-44; 1984
  A. Tissue Preparation (Prepare all Solutions on Ice)
  1. Thaw frozen brains from male Guinea Pigs (in assay buffer) and place in 50 mM TRIS-HCl (pH 7.4 at 25° C. with 120 mM NaCl). Isolate striatum.
  2. Use a Polytron to homogenize tissue in 20 vols. (w/v) of 50 mM Tris-HCl (pH 7.4 at 25° C. with 120 mM NaCl).
  3. Centrifuge homogenate at 48,400×g for approximately 10 minutes at 4° C. Discard supernatant.
  4. Wash pellet an additional time as described in steps 2 and 3.
  5. Store pellet on ice until needed for binding assay.
  6. Using a Polytron (setting 5; approximately 10 seconds) resuspend pellet in 50 mM Tris-HCl (pH 7.4 at 25° C. with 120 mM NaCl) to an initial concentration of 10 mg/ml (original wet weight), such that the final concentration is 8 mg/ml or 4.0 mg tissue/tube.
  B. Binding Reaction
  1. Each tube receives the following components:
    50 ul drug or vehicle
    50 ul [3H]-WIN 35,428
    400 ul tissue suspension.
  2. Initiate binding reaction with the addition of tissue, and incubate for 120 minutes at 0° C. (on ice).
  3. Terminate binding reaction by rapid filtration of tube contents onto untreated Whatman GF/C filters.
  4. Rinse the assay tubes once with ice cold 50 mM TRIS HCl (pH 7.4 at 25° C. with 120 mM NaCl, BSA), then rapidly rinse the filters with 6×1 mls/tube of the same wash buffer.
  5. Radioactivity trapped onto the filters is assessed using LSM machine. Let sit for 3 hours in scint cocktail.
  C. Dopamine Transporter Binding Assay
  Materials and Reagents
  1. [3H]-WIN 35-428 is diluted to a concentration of 60 nM in 50 mM TRIS HCl (pH 7.4 at 25° C. with 120 mM NaCl). Thus, the final ligand concentration is 6 nM.
  2. Non-specific binding is defined as that remaining in the presence of 1×10-6 M GBR12909 (room temperature cabinet). GBR12909 MW=523.5 g/mol. Will solubilize in 4% DMSO (sonicate 15 minutes). Aliquots can be used (1E-3).
  3. The reference compound for the assay is GBR12909 and is diluted in 4% DMSO and is then run at the following final concentrations: $1\times10^{-10}$, $5\times10^{-10}$, $2\times10^{-9}$, $5\times10^{-9}$, $1\times10^{-8}$, $2\times10^{-8}$, $5\times10^{-8}$, $1\times10^{-7}$, $2\times10^{-7}$, $5\times10^{-7}$, $1\times10^{-6}$, $5\times10^{-6}$.
  4. The positive control GBR12909 and is run at the final concentrations of: 2×10-8, $1\times10^{-7}$, $5\times10^{-7}$M.
  5. The $K_d$ for the receptor is 28.0 nM.

Buffers

| Assay Buffer | 1 L | 2 L | 3 L | 4 L |
|---|---|---|---|---|
| 50 mM Tris-HCl pH 7.4 | 6.06 g | 12.12 g | 18.18 g | 24.24 |
| 120 mM NaCl | 7.01 g | 14.02 g | 21.03 g | 28.04 g |

Wash Buffer (Add 1 g BSA/1L Assay Buffer)

| 50 mM Tris-HCl pH 7.4 | 24.2 g/4 L |
|---|---|
| 120 mM NaCl | 28.0 g/4 L |
| BSA | 4 g/4 L |

Ki: 2.25-22.5 e−9

II: Norepinephrine Transporter (Human Recombinant) Binding Assay

This assay was carried out in accordance with the procedure described by Raisman, R, et al. *Eur. Jrnl. Pharmacol.* 78: 345-351 (1982) with modifications. See also, Langer, S., et al., *Eur. Jrnl. Pharmacol,* 72: 423-4 (1981).

Tissue Preparation 1. hrNET (Receptor Biology; RBNET) is diluted in assay buffer to 2.5 microunits/ml, so that each tube receives 0.5 microunits, or 2 microunits/ml.

NOTE: 100 microassays, add 20 mls of buffer.

Binding Reaction

1. Each tube receives the following components:
   25 ul drug or vehicle
   25 ul [$^3$H]-Nisoxetine
   200 ul tissue suspension.
2. Initiate binding reaction with the addition of tissue, and incubate at room temperature for 1 hour.
3. Terminate binding reaction by rapid filtration of tube contents onto 0.1% PEI treated GF/C filters (TopCount).
4. Rinse the assay tubes once with ice cold 50 mM NaCl, then rapidly rinse the filters with 6×1 ml/tube of the same wash buffer.
5. Radioactivity trapped onto the filters is assessed using liquid scintillation spectrophotometer after soaking the filters for at least 1 hour in scintillation cocktail.

Materials and Reagents

1. The receptor source is human recombinant/CHO.
2. [$^3$H]-Nisoxetine, diluted to a concentration of 10 nM in assay buffer, is used as the radioligand. Thus, the final ligand concentration is 1 nM.
3. Non specific binding is defined as that remaining in the presence of $1\times10^{-6}$M desipramine (MW=302.8) (Make fresh: in bag with dessicating rocks 1, dissolves in water 1E-3).
4. The reference compound for the assay is desipramine. Desimpramine is run at following final concentrations:
   $1\times10^{-10}$, $2\times10^{-10}$, $5\times10^{-10}$, $1\times10^{-9}$, $2\times10^{-9}$, $5\times10^{-9}$, $1\times10^{-8}$, $2\times10^{-8}$, $5\times10^{-8}$, $1\times10^{-7}$, $2\times10^{-7}$, $5\times10^{-7}$M
5. The positive control is any of the above run at the final concentrations of:
   $1\times10^{-9}$, $5\times10^{-9}$, $2\times10^{-8}$ M.
6. The $K_d$ for the receptor is 3 nM.

Buffers

|  | MW (g/mole) | g/1 L |
|---|---|---|
| Incubation Buffer: | | |
| 50 mM Tris, pH 7.4 | 121 | 6.06 |
| 5 mM KCl | 74.6 | 0.38 |
| 120 mM NaCl | 58.4 | 7.02 |
| Wash Buffer: | | |
| 50 mM NaCl | 58.4 | 3.0 |

The results of the DAT and NET binding assays are set forth in the following table:

| Ex. No. | Name | Structure | INH at 10 μM DAT | INH at 10 μM NET | Ki DAT |
|---|---|---|---|---|---|
| 1 | 3-(benzyl)-syndonimine-N-phenylcarbamoyl | 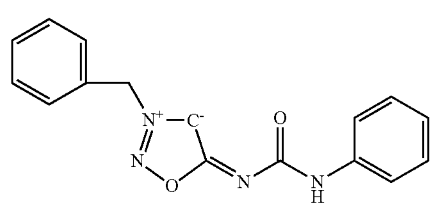 | 90% | 0% | 36 nM |
| 2 | 3-(p-carboxylbenzyl)-syndonimine N-phenylcarbamoyl | 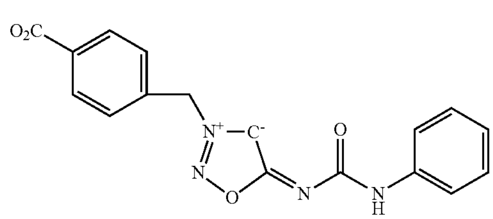 | 92% | 11% | 2.7 nM |

-continued

| Ex. No. | Name | Structure | INH at 10 µM DAT | INH at 10 µM NET | Ki DAT |
|---|---|---|---|---|---|
| 3 | 3-(p-methyl-benzyl)-syndonimine-N-phenylcarbamoyl | 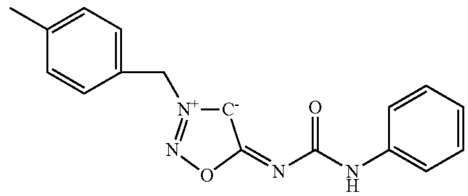 | 94% | 14% | 0.19 nM |
| 4 | 3-phenethyl-syndonimine-N-(3',4'-dichlorophenyl)carbamoyl | 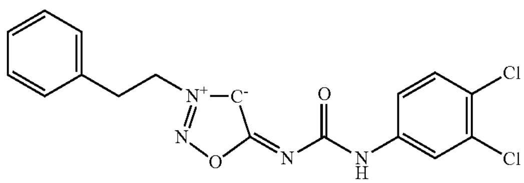 | 99% | 2% | 40 nM |
| 5 | 3-(p-nitrophenethyl)syndonimine-N-(3',4'-dinitrophenyl)carbamoyl | 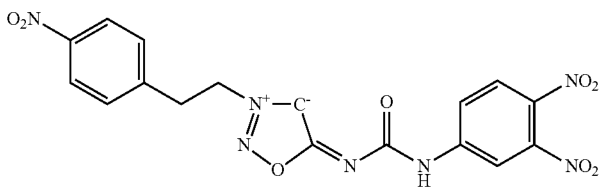 | 85% | 4% | 100 nM |
| 6 | 3-(phenylpropyl)-syndonimine-N-phenylcarbamoyl | 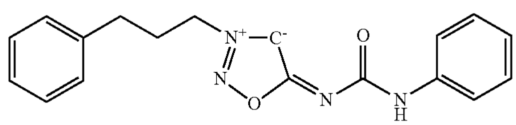 | 96% | 1.44% | 25 nM |
| 7 | 3-(p-fluorobenzyl)-syndonimine-N-phenylcarbamoyl | 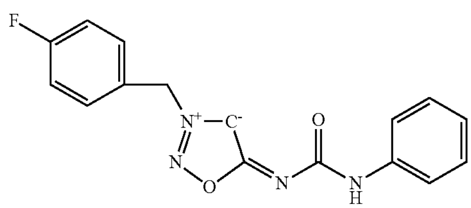 | 99% | 15% | 0.46 nM |

Preferred compounds of the invention have a DAT binding inhibition (at 10 µm) of greater than or equal to 90% and a NET binding inhibition (at 10 µM) of less than or equal to 15%; or a ratio of DAT:NET binding inhibition (at 10 µM) of at least 9:1.

EXAMPLE 9

The following materials and methods are provided to facilitate the practice of Example 9, in which drug concentration in certain biological samples were assessed using different routes of administration.
Parameters Used in Dosing and Drug Administration of the Compound of Example 3:

| Dose route | Dose range | Dose volume |
|---|---|---|
| | | (Use a 1-ml syringe with appropriate oral feeding needle.) |
| i.v. | 10 mg/kg | 5-10 × bodyweight (5-10 ml/kg, i.e. a 25 g mouse receives 125-250 ul) |

-continued

| Dose route | Dose range | Dose volume |
|---|---|---|
| i.p | 10 mg/kg | 10 × bodyweight |
| Oral | 10, 30 mg/kg | 10 × bodyweight |

Mouse Strain
  Adult C57BL/6 mice (preferred 16 weeks old).
Time Point
  Pre-dose, 5, 15, 30, 60, 120, 240 and 480 mins for IV.
  Pre-dose, 15, 30, 60, 120, 240, 480 and 1,440 mins for IP and oral.
  Three mice per time point. If all three routes are conducted in same day, one group of pre-dose is efficient.
Dosing Formula
  10% EtOH
  0.05-0.08% 7.5N HCL
  30% Captisol in Saline
  Final PH at 2.5-3

EXAMPLE 10

Spontaneous Locomotor Activity (Open Field Study)

A dose response study was conducted of locomotor depression induced by the compound of Example 3, according to NIDA's Medication Development Division (MDD) locomotor activity studies standard protocol. The study was conducted using 40 Digiscan locomotor activity testing chambers (40.5×40.5×30.5 cm) housed in sets of two, within sound attenuating chambers. A panel of infrared beams (16 beams) and corresponding photodetectors were located in the horizontal direction along the sides of each activity chamber. A 7.5 W incandescent light above each chamber provided dim illumination. Fans provided an 80 dB ambient noise level within the chamber. Separate groups of 8 non-habituated male Swiss Webster mice (Hsd:ND4, aged 2-3 months) were injected via the intraperitoneal (IP) route with either vehicle (2% methyl cellulose) or the compound of Example 3, above, (3, 10, 30 or 100 mg/kg) twenty minutes prior to locomotor activity testing. Just piro to placement in the apparatus, all mice received a saline injection IP. In all studies, horizontal activity (interruption of photocell beams) was measured for 1 hour within 10 minute periods. Testing was conducted with one mouse per activity chamber.

The same protocol was followed in a study of locomotor depression induced by the compound of Example 6.

EXAMPLE 11

Time-Course (8 Hr.) Mouse Locomotor Activity Testing

A time course/dose response study of the locomotor depression inducing effect of the compound of Example 3 was conducted, according to the same MDD locomotor activity studies time course protocol described immediately above, except that groups of 8 mice were injected with either vehicle (2% methylcellulose) or the compound of Example 3 (3, 10, 30 or 100 mg/kg), immediately prior to locomotor activity testing. Behavioral observations were recorded on each mouse at 30, 120 and 480 minutes following 100 mg/kg of the test compound. The vehicle used in this study was 2% methylcellulose.

A separate time course/dose response study of the locomotor depression inducing effect of the compound of Example 6 was also conducted, under the same conditions described above for testing of the compound of Example 3. Additional groups of 8 mice were injected with either vehicle (2% methylcellulose) or the test compound (3, 10, 30 or 100 mg/kg), immediately prior to locomotor activity testing. Behavioral observations were recorded on each mouse at 30, 120 and 480 minutes following 100 mg/kg of the test compound. The vehicle used in this study was 2% methylcellulose.

Results

The inventors have identified DAT selective inhibitors for use in the treatment and prevention of cocaine abuse and other disorders associated with aberrant dopamine reuptake. Two such inhibitors, namely, the compounds of Examples 3 and 6, above, are well tolerated up to at least 200 mg/kg. Observable changes in behavior occurred in minutes and lasted for about 2-3 hours. Notably subjects treated with the compound of Example 3 became lethargic at dosages above 125 kg/mg, whereas this effect was reduced at higher concentrations of the compound of Example 6.

In the studies using adult C57BL/6 mice (preferably approximately 16 weeks old), dosing and drug administration parameters for the compound of Example 3 were explored. Table 2 summarizes the results of these studies. Clearly, the compound is suitable for oral administration and lasts in the plasma up to 2-3 hours. Moreover, the compound of Example 3 reaches the brain whether administered orally or via intravenous administration. See Table 3.

TABLE 2

Plasma Concentration (ng/mL) by Different Routes of Drug Administration

| Time | 10 mg/kg (IV) | 10 mg/kg (IP) | 10 mg/kg (PO) | 30 mg/kg (PO) |
|---|---|---|---|---|
| 0 | 18.33 | 21.00 | 10.60 | 8.93 |
| 5 | 2091.03 | 973.00 | 218.50 | 837.87 |
| 15 | 2110.87 | 315.97 | 115.45 | 669.80 |
| 30 | 915.00 | 544.25 | 59.90 | 374.53 |
| 60 | 416.63 | 115.40 | 21.30 | 113.87 |
| 120 | 139.27 | 82.47 | 17.57 | 41.87 |
| 240 | 47.43 | 34.03 | 15.80 | 48.53 |
| 480 | 94.63 | 31.20 | 14.30 | 13.40 |

TABLE 3

Brain Drug Concentration (ng/mL) by Different Routes of Drug Administration

| Time | 10 mg/kg (IV) | 10 mg/kg (IP) | 10 mg/kg (PO) | 30 mg/kg (PO) |
|---|---|---|---|---|
| 0 | 95.10 | 0.00 | 107.55 | 123.97 |
| 5 | 2313.10 | 1456.65 | 417.80 | 868.87 |
| 15 | 1723.27 | 374.43 | 297.60 | 844.87 |
| 30 | 1139.30 | 242.00 | 149.93 | 626.63 |
| 60 | 464.40 | 189.93 | 158.00 | 217.60 |
| 120 | 78.70 | 70.20 | 165.13 | 203.07 |
| 240 | 177.87 | 143.13 | 97.47 | 183.03 |
| 480 | 48.95 | 122.95 | 163.00 | 168.35 |

Additional pharmacokinetic studies were performed, as shown in FIGS. 2A-2D. It appears that the compound of Example 6 exhibits slightly better bioavailability in the plasma and brain when compared to the compound of Example 3 at the same dosage. The compound of Example 6 also exhibits relatively higher oral bioavailability when administered at different dosages. See FIG. 3.

The spontaneous locomotor activity assessments were performed following administration of the DAT inhibitors of the present invention according to the procedure described in Tella et al. (1996) Pharmacol Biochem. Behav. 54:343-54; Elmer et al. (1996) Pharmacol Biochem Behav 53:911-918. The results of these assessments appear in FIGS. 4 and 5. FIGS. 4A and 4B are graphs that show that the compound of Example 3 demonstrates a dose dependent suppression of spontaneous locomotor activity. The compound of Example 6 showed a similar dose dependent response, as can be seen in FIGS. 5A and 5B.

The results of the above-described time-course mouse locomotor activity experiment using the compound of Example 3 are set forth in FIG. 6A, which shows average horizontal activity counts/10 min as a function of time (0-8 hr) and dose of the compound (top to bottom panels). Treatment with this compound resulted in time- and dose-dependent depression of locomotor activity following 30 and 100 mg/kg. Depressant effects of 30 and 100 mg/kg occurred within 10 minutes following injection and lasted 140 to 160 minutes. The period 20-50 min was selected for analysis of dose-response data because this was the time period in which maximal suppression first appeared as a function of dose. The mean average horizontal activity counts/10 min for this 30-min period were fit to a linear function of $\log_{10}$ dose of the descending portion of the dose-effect curve (3 to 100 mg/kg dose range). The $ID_{50}$ (dose producing ½ maximal depressant activity, where maximal depression=0 counts/30 mint) was estimated to be 24.0 mg/kg.

A two-way analysis of variance conducted on horizontal activity counts/10 min indicated a significant effect for Treatment $F(4,35)=5.35$, $p=0.002$, 10-Minute Periods $F(47, 1645)=42.63$, $p<0.001$, and for the interaction of Periods and Treatment $F(188,1645)=2.26$, $p<0.001$. A one-way analysis of variance conducted on $\log_{10}$ horizontal activity counts for the 20-50 min time period (maximal depressant effect) indicated a significant effect of Treatment $F(4,35)$-27.59, $p<0.001$, and planned comparisons (a priori contrast) against the vehicle group showed a significant depressant effect for 30 and 100 mg/kg ($ps<0.05$ denoted on FIG. 6A with an asterisk).

The results of the time-course mouse locomotor activity experiment using the compound of Example 6, is provided in FIG. 6B, which shows average horizontal activity counts/10 min as a function of time (0-8 hr) and dose of the test compound (top to bottom panels). Treatment with this compound resulted in time-dependent depression of locomotor activity following 100 mg/kg. Depressant effects of 100 mg/kg occurred within 10 minutes following injection and lasted 160 minutes. The period 50-80 min was selected for analysis of dose-response data because this was the time period in which maximal suppression first appeared as a function of dose. The mean average horizontal activity counts/10 min for this 30-min period were fit to a linear function of $\log_{10}$ dose of the descending portion of the dose-effect curve (10 to 100 mg/kg dose range). The $ID_{50}$ (dose producing ½ maximal depressant activity, where maximal depression=0 counts/30 min) was estimated to be 30.2 mg/kg.

A two-way analysis of variance conducted on horizontal activity counts/10 min indicated a significant effect of Treatment $F(4,35)=6.84$, $p<0.001$, 10-Minute Periods $F(47, 1645)=48.92$, $p<0.001$, and the interaction of Periods and Treatment $F(188,1645)=1.64$, $p<0.001$. A one-way analysis of variance conducted on log 10 horizontal activity counts for the 50-80 min time period (maximal depressant effect) indicated a significant effect of Treatment $F(4,35)=6.01$, $p=0.001$, and planned comparisons (a priori contrast) against the vehicle group showed a significant depressant effect for 100 mg/kg ($ps<0.05$ denoted on FIG. 6B with an asterisk).

To further characterize the pharmacological effects of these compounds, Irwin behavioral battery testing was performed.

Testing occurred towards the end of the light cycle between 8-11 a.m. (lights go off at 11:00 a.m.). The mice were acclimated to the testing room for at least 30 minutes. The Irwin test equipment (timer, viewing jar and support, open arena, grid, ruler, sound box, wood stocks, kimwipes box) was placed under a laminar flow hood. The mouse was first placed in the viewing jar for five (5) minutes and the following parameters were scored:

1. General appearance—coat quality, whiskers
2. Body position
3. Spontaneous activity
4. Respiration rate
5. Tremors
6. Twitches
7. Bizarre behavior—comments
8. Convulsions
9. Defecation—number of feces at the end of the session At the end of the 5-minute period, the viewing jar with the muose in it was transferred to the arena, where the jar was disassembled and the mouse released into the arena. The mouse was not handled by the experimenter. The following parameters were scored in the arena in the following order:

1. Transfer arousal—during the 10 first seconds
2. Locomotor activity—number of squares entered by all four feet in 30 seconds
3. Palpebral closure
4. Piloerection
5. Startle response—90 dB sound from clickbox 30 cm above arena
6. Gait
7. Pelvic elevation
8. Tail elevation—during forward motion
9. Touch escape—finger stroke from above
10. Tail pinch—with forceps 3 cm from the base of tail
11. Body temperature—hypo- or hyperthermia
12. Positional passivity—struggle response to sequential handling by tail, neck, hind legs, or held supine Then the mouse was picked up by its tail and kept above the arena to score the following set of parameters:

1. Trunk curl
2. Limb grasping
3. Visual placing—extension of forelimbs when animal is lowered by base of tail from a height of 15 cm above a wire grid
4. Grip strength—mouse is lowered and allowed to grip the grid; gentle horizontal backwards pull is applied
5. Body tone—sides of mouse are compressed between thumb and index finger
6. Pinna reflex—mouse is gently restrained on grid and the proximal part of the inner cathus is touched lightly with the tip of fine wire probe; ear retraction is observed
7. Corneal reflex—mouse is gently restrained no grid and the cornea is touched lightly with the side of fine wire probe; eye-blink response is observed
8. Toe pinch—the mid digit of hind foot is gently compressed laterally with fine forceps. The hind limbs are lifted clear of the grid
9. Wire Maneuver—mouse is held above the wire by tail suspension and lowered to allow the forelimbs to grip the horizontal wire; the mouse is held in extension and rotated around to the horizontal and released The mouse was then placed in supine restraint to score the below parameters in the following order:

1. Body length—from tip of nose to base of tail (mm)
2. Skin color—plantar surface and digits of forelimbs
3. Heart rate—felt by palpation below sternum
4. Limb tone—resistance to gentle finger tip pressure on plantar surface of left/right hind paw
6. Lacrimation
7. Pupil reflex 8. Salivation 9. Provoked biting—dowel rod gently inserted between the teeth at the side of the animal's mouth 10. Irritability The final three parameters were scored with the mouse above or in the arena:

1. Righting reflex—mouse is held by the tail and flicked backgrounds through the air such that it performs a backward somersault when released; the landing position is observed 2. Contact righting reflex—mouse is placed into a plastic tube and turned upside down 3. Negative geotaxis—mouse is placed no horizontal grid; the grid is raised to vertical with mouse facing the floor; behavior is observed for 30 seconds Experimental Design for Irwin Behavorial Battery

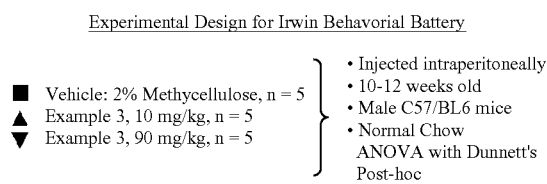

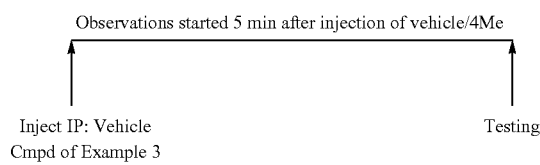

The test results presented in FIGS. 7A-7C demonstrate that the compound of Example 3 induced significant behavioral effects in the Irwin Behavioral Batter. FIG. 7A shows the results on spontaneous activity. FIG. 7B shows the results on grip strength. FIG. 7C shows the effects of the compound administration on limb tone.

Open Field testing was also performed. In carrying out this testing, individually housed male and female mice aged 8-12 weeks were used. The mice were maintained on a reverse L:D/12 p.m.: 12 a.m. cycle in a barrier facility. Food and water were available ad libitum. Testing occurred towards the end of the light cycle between 6-12 a.m. Mice were acclimated to the testing room for at least 30 minutes. The assay was performed in a custom-made Open Field Apparatus. Each chamber was a 50 by 50 cm square. The experiment was recorded and tracked by a tracking system obtained from Viewpoint.

The time and the path length in the center of the open field were determined. The center of the open field is defined as a 13.5×13.5 cm square in the geometric center of the arena. The percent of path in the center is calculated as $$\frac{\text{Path length in the center}}{\text{Total path length}} \times 100\%$$

For each mouse, the total path length and path length for 60 minutes at 5 minute intervals was determined as a measure of locomotor activity. In addition, feces produced by each experimental animal during the test was counted. Each chamber was cleaned between individual mouse testing.

Path length for 60 minutes at 5 minute intervals was analyzed by repeat measures using SPSS software. All other parameters were compared using unpaired t-test (GraphPad Prism).

Experimental Design for Open Field

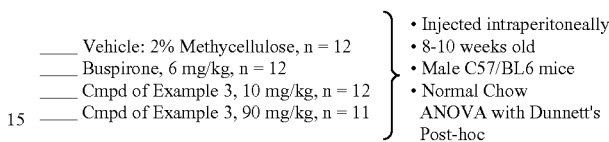

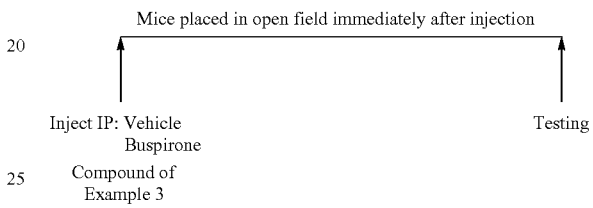

The data presented in FIG. 8 demonstrates that the compound of Example 3 is effective to reduce locomotor activity in open field testing. In yet another assay, the same compound produced demonstrable anxiolytic effects. See FIGS. 9A-9D.

Novel environment-induced feeding suppression (NEIFS) testing was also performed. Individually housed male mice aged 8-12 weeks are used for this testing. Mice were maintained no a reverse L:D/12 p.m.:12 a.m. cycle in a barrier facility with food and water available ad libitum. Testing occurred towards the end of the light cycle between 6-12 a.m. The mice were acclimated to the testing room for at least 30 minutes.

Days 1, 2, 3 and 5 (Home cage): A Petri dish containing crushed Graham crackers was placed in the farthest corner from each mouse in its own home cage. The time to approach (defined as nose of the mouse directed at or within 1 cm of the dish) and consume (eat, not pick up) the crackers was recorded immediately following the placement of the dish into home cage.

Day 4 (Novel environment): The procedure followed was the same as described for home cage; however, on day 4 the mouse was placed in a new cage with bedding (novel environment) for the duration of the experiment. The mice were subsequently returned to their respective home cages for day 5 testing. The remaining crackers and Petri dish were disposed of at the end of the experiment for each mouse.

In a novel environment induced feeding suppression assay, the compound of Example 3 induced measurable anxiolytic effects. See FIG. 10. Notably, the compound had no effect on the number of fecal boli in open field testing.

Rotarod assays were also performed using the experimental protocol and design set forth below. Individually housed male mice aged 8-12 weeks were used for this experiment. Mice were maintained on a reverse L:D/12 p.m.: 12 a.m. cycle in a barrier facility with food and water available ad libitum. Testing occurred towards the end of the light cycle between 6-12 a.m. Mice were acclimated to the testing room for at least 30 minutes.

The assay was carried out using four EzRod test chambers kept in a laminar hood for testing. For the accelerating rotarod paradigm, mice were given 10 trials with the maximum duration of 3 minute and a 30-second intertrial interval (ITI). Each mouse was placed on the EZRod machines and the latency to fall was recorded for all trials. If the mouse fell or 3 minutes elapsed, the mouse was left in the bottom of the EzRod test chamber for 30 seconds before starting the next trial.

The latency to fall was compared between the two groups by analysis of variance (ANOVA) with repeated measures.

Experimental Design for Rotarod

____ Vehicle: 2% Methycellulose, n = 10
____ 20% Ethanol, 1.5 mg/kg, n = 10
____ Cmpd of Example 3, 10 mg/kg, n = 10
____ Cmpd of Example 3, 90 mg/kg, n = 10

• Injected intraperitoneally
• 9-11 weeks old
• Male C57/BL6 mice
• Normal Chow
  ANOVA with Dunnett's Post-hoc Mice placed on Rotarod 5 min after injection of vehicle/4Me and 30 min after ethanol Inject IP: Vehicle       Testing
  20% Ethanol
Cmpd of Example 3

The data presented in FIG. 11 reveal that the compound of Example 3 did not affect rotarod performance.

The foregoing specification includes citations to certain patent and literature references, which are provided to indicate the state of the art to which this invention pertains. The entire disclosure of each of the cited references is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A method of managing and/or delaying the progression of a disorder alleviated by inhibiting dopamine reuptake in a patient in need thereof, wherein said disorder is autism, the method comprising administering to said patient a therapeutically effective amount of at least one compound having the formula:

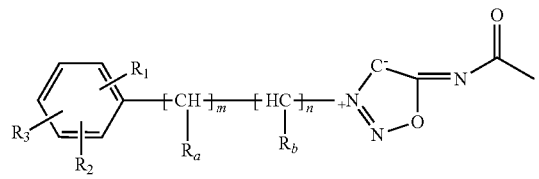

-continued

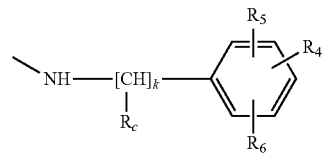

wherein $R_1$, $R_2$, $R_3$, $R_4$, $R_5$ and $R_6$, independently of one another, are radicals selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl, said alkyl, alkenyl, alkynyl or cycloalkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$ alkoxy group, said aryl and aralkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$ alkoxy group;

$R_a$, $R_b$ and $R_c$, independently of one another, represent radicals selected from H, $C_1$-$C_4$ alkyl, phenyl or phenyl $C_1$-$C_4$ alkyl, said alkyl radical, said phenyl radical and said phenyl $C_1$-$C_4$ alkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$ alkoxy group;

m, n and k are independent integers from 0-4, except that m+n ≠0, and $R_b$ ≠alkyl when m+n=2; or a pharmaceutically acceptable salt of said compound.

2. The method according to claim 1, wherein the compound administered is selected from the group consisting of 3-(p-methylbenzyl)-sydnonimine-N-phenylcarbamoyl and 3-(phenylpropyl)-sydnonimine-N-phenylcarbamoyl, and a pharmaceutically acceptable salt of said compound.

3. The method according to claim 1, wherein said compound is administered in dosage unit form, said dosage unit containing from about 0.01 to about 200 mg of said compound per kilogram of patient body weight per day.

4. The method according to claim 3, wherein said dosage unit includes a pharmaceutically acceptable vehicle.

5. The method according to claim 1, wherein said compound is administered orally.

6. The method according to claim 1, wherein said compound is administered parenterally.

7. A method of managing and/or delaying the progression of a condition or disease state by modulating dopamine reuptake activity, wherein the condition or disease state is autism, said method comprising administering to a patient having the condition or disease state a therapeutically effective amount of at least one compound having the formula:

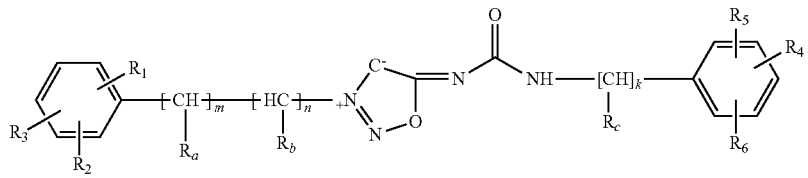

wherein $R_1$, $R_2$, $R_3$, $R_4$, $R_5$ and $R_6$, independently of one another, are radicals selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl, said alkyl, alkenyl, alkynyl or cycloalkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$ alkoxy group, said aryl and aralkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$alkoxy group;

$R_a$, $R_b$ and $R_c$, independently of one another, represent radicals selected from H, $C_1$-$C_4$ alkyl, phenyl or phenyl $C_1$-$C_4$ alkyl, said alkyl radical, said phenyl radical and said phenyl $C_1$-$C_4$ alkyl radical being optionally substituted by at least one halogen, OH, SH, $NH_2$, $C_1$-$C_4$ alkylamino, $C_1$-$C_4$ dialkylamino, COOH, CN, $NO_2$, $C_1$-$C_4$ alkyl or $C_1$-$C_4$ alkoxy group;

m, n and k are independent integers from 0-4, except that m+n $\neq$0, and $R_b$ $\neq$alkyl when m+n=2; or a pharmaceutically acceptable salt of said compound; said compound having dopamine transporter protein-specific inhibitory activity and locomotor suppressant activity.

8. A method of easing the symptoms and/or effects of autism by inhibiting dopamine reuptake transporter (DAT) activity in a patient in need thereof, the method comprising administering to said patient a therapeutically effective amount of a selective DAT inhibitor; wherein the selective DAT inhibitor exhibits DAT binding inhibition of greater than or equal to 90% at 10 μM and a norepinephrine transporter (NET) binding inhibition of less than or equal 15% at 10 μM, wherein the selective DAT inhibitor is selected from the group consisting of 3-(p-methylbenzyl)-sydnonimine-N-phenylcarbamoyl and 3-(phenylpropyl)-sydnonimine-N-phenylcarbamoyl, and a pharmaceutically acceptable salt of said selective DAT inhibitor.

9. A method of managing and/or delaying the progression of a disorder alleviated by inhibiting dopamine reuptake in a patient in need thereof, wherein said disorder is autism, the method comprising administering to said patient a therapeutically effective amount of at least one compound selected from the group consisting of 3-(p-methyl-benzyl)-syndonimine-N-phenylcarbamoyl, 3-(p-carboxyl-benzyl)-sydnonimine-N-phenylcarbamoyl, 3-(p-fluoro-benzyl)-sydnonimine-N-phenylcarbamoyl, and 3-(phenylpropyl)-sydnonimine-N-phenylcarbamoyl, and a pharmaceutically acceptable salt of said compound.

10. The method of claim 1, wherein the compound administered comprises 3-(phenylpropyl)-sydnonimine-N-phenylcarbamoyl or a pharmaceutically acceptable salt of said compound.

11. The method of claim 8, wherein the selective DAT inhibitor is 3-(phenylpropyl)-sydnonimine-N-phenylcarbamoyl or a pharmaceutically acceptable salt of said selective DAT inhibitor.

* * * * *